(12) United States Patent
Saitou et al.

(10) Patent No.: US 7,781,960 B2
(45) Date of Patent: Aug. 24, 2010

(54) METAL COMPLEX COMPOUND AND ORGANIC ELECTROLUMINESCENT ELEMENT USING THE SAME

(75) Inventors: Masatoshi Saitou, Chiba (JP); Hidetsugu Ikeda, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 269 days.

(21) Appl. No.: 11/813,516

(22) PCT Filed: Dec. 28, 2005

(86) PCT No.: PCT/JP2005/024079

§ 371 (c)(1), (2), (4) Date: Jul. 9, 2007

(87) PCT Pub. No.: WO2006/073112

PCT Pub. Date: Jul. 13, 2006

(65) Prior Publication Data

US 2008/0061684 A1 Mar. 13, 2008

(30) Foreign Application Priority Data

Jan. 7, 2005 (JP) ............................. 2005-002480

(51) Int. Cl.
*H01L 51/54* (2006.01)
*C07F 15/00* (2006.01)
*C07D 213/02* (2006.01)
*C07D 231/00* (2006.01)

(52) U.S. Cl. ........................... 313/504; 546/4; 548/106

(58) Field of Classification Search ................. 313/504; 546/4; 548/106
See application file for complete search history.

(56) References Cited

U.S. PATENT DOCUMENTS

| 6,097,147 A | 8/2000 | Baldo et al. |
| 2001/0025108 A1 | 9/2001 | Phillips |
| 2002/0182441 A1 | 12/2002 | Lamansky et al. |

FOREIGN PATENT DOCUMENTS

| JP | 3-200889 | 9/1991 |
| JP | 7-138561 | 5/1995 |
| JP | 8-239655 | 9/1996 |
| JP | 2002-170684 | 6/2002 |
| JP | 2003 81989 | 3/2003 |
| JP | 2003-123982 | 4/2003 |
| JP | 2003-133074 | 5/2003 |
| JP | 2003 515897 | 5/2003 |
| JP | 2004 259529 | 9/2004 |
| WO | WO 01/41512 A1 | 6/2001 |
| WO | 2006 000544 | 1/2006 |

OTHER PUBLICATIONS

Ana P. Martinez, et al., "The Rhodium and Iridium Co-Ordination Chemistry of the Hemilabile Hybrid Ligand 1-(2'-Pyridyl)-3-Dimethylamino-2-Propen-1-One", Inorganica Chimica Acta, Vol. 347, pp. 86-98, 2003.

(Continued)

*Primary Examiner*—Joseph R Kosack
(74) *Attorney, Agent, or Firm*—Oblon, Spivak, McClelland, Maier & Neustadt, L.L.P.

(57) ABSTRACT

The present invention provides a novel metal complex compound represented by the following general formula (1), and an organic electroluminescence element which has a high efficiency of light emission and a long lifetime, wherein one of organic thin film layers including at least a light emitting layer between an anode and a cathode, at least one of the organic thin film layers contains the metal complex compounds.

$$(L_1)_m M(L_2)_n \qquad (1)$$

wherein M represents Ir, Pt and Rh; $L_1$ and $L_2$ represents mutually different bidentate ligands; $(L_1)_m M$ as a partial structure is represented by general formula (2) and $M(L_2)_n$ as a partial structure is represented by general formula (3): and m and n are each an integer of 1 or 2, provided that m+n is a integer of 2 or 3.

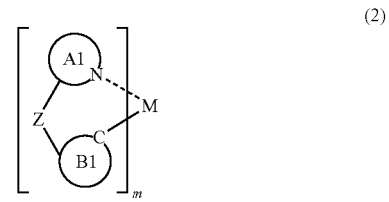

(2)

wherein ring A1 represents an aromatic hetrocyclic ring group; and ring B1 represents an aryl group, provided that the ring A1 and the ring B1 are covalently linked to each other via Z which represents a single bond or the like.

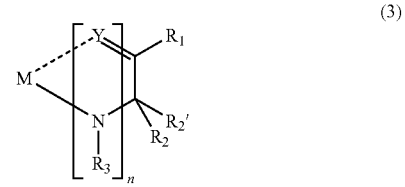

(3)

wherein $R_1$, $R_2$, $R_2'$ and $R_3$ each independently represent an alkyl group or the like; $R_1$ and $R_2$, $R_1$ and $R_2'$, $R_2$ and $R_2'$, $R_2$ and $R_3$, and $R_2'$ and $R_3$ may combine with each other to form a cyclic structure; and Y represents a group represented by O or S.

6 Claims, No Drawings

OTHER PUBLICATIONS

Cyril Godard, et al., "Dipyridylketone Binding and Subsequent C-C Bond Insertion Reactions at Cyclopentadienylrhodium", Chemical Communications, No. 18, pp. 2332-2333, 2003.

C. W. Tang, et al., "Organic electroluminescent diodes", Appl. Phys. Lett., vol. 51, No. 12, Sep. 21, 1987, pp. 913-915.

F. D. O'Brien, et al., "Improved energy transfer in electrophosphorescent devices", Applied Physics Letters, vol. 74, No. 3, Jan. 18, 1999, pp. 442-444.

M. A. Baldo, et al., "Very high-efficiency green organic light-emitting devices based on electrophosphorescence", Applied Physics Letters, vol. 75, No. 1, Jul. 5, 1999, pp. 4-7.

METAL COMPLEX COMPOUND AND ORGANIC ELECTROLUMINESCENT ELEMENT USING THE SAME

TECHNICAL FIELD

The present invention relates to a metal complex compound and an organic electroluminescence device using the same, in particular, to an organic electroluminescence device having a high efficiency of light emission and a long lifetime, and a novel metal complex compound for producing the electroluminescence device.

BACKGROUND ART

An organic electroluminescence ("electroluminescence" will be occasionally referred to as "EL", hereinafter) device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used a laminate structure using tris(8-quinolinolato)aluminum for the light emitting layer and a triphenyldiamine derivative for the hole transporting layer. Advantages of the laminate structure are that the efficiency of hole injection into the light emitting layer can be increased, and that the efficiency of forming excitons which are formed by blocking and recombining electrons injected from the cathode can be increased, and that excitons formed among the light emitting layer can be enclosed. As the structure of the organic EL device, a two-layered structure having a hole transporting (injecting) layer and an electron transporting and light emitting layer or a three-layered structure having a hole transporting (injecting) layer, a light emitting layer and an electron transporting (injecting) layer are well known. To increase the efficiency of recombination of injected holes and electrons in the devices of the laminate type, the structure of the device and the process for producing the device have been studied.

As the light emitting material of the organic EL device, chelate complexes such as tris(8-quinolinolato)aluminum, coumarine derivatives, tetraphenylbutadiene derivatives, bis-styrylarylene derivatives and oxadiazole derivatives are known. It is reported that light in the visible region ranging from blue light to red light can be obtained by using these light emitting materials, and development of a device exhibiting color images is expected (refer to, for example, Patent literatures 1, 2, and 3).

In addition, it has been recently proposed that an organic phosphorescent material is applied to a light emitting layer besides a light emitting material (refer to, for example, non-Patent literatures 1 and 2). A high efficiency of light emission has been achieved by utilizing a singlet state and a triplet state of the organic phosphorescent materials in a light emitting layer of an organic EL device. Since it has been considered that singlet exciton and triplet exciton are formed at a ratio of 1 to 3 due to difference of spin multiplicity thereof on recombination of electrons and holes in an organic EL device, it should be understood that three to four times higher efficiency of light emission can be achieved by utilizing an phosphorescent light emitting material than by utilizing only a fluorescent light emitting material.

In the above organic EL devices, in order to avoid quenching of triplet excited state or excitons in triplet state, a construction comprised by laminating sequentially an anode, a hole transporting layer, an organic light emitting layer, an electron transporting layer (a hole blocking layer), an electron transporting layer, a cathode and so forth has been employed, and a host compound and a phosphorescent compound have been employed as an organic light emitting layer (refer to, for example, Patent literatures 4 and 5). The patent literatures relate to an organic phosphorescent material emitting a light in the range of from red to green. In addition, technologies relating to a material emitting a blue light are disclosed (refer to, for example, Patent literatures 6, 7 and 8). However, these have very short lifetimes Ligand-frameworks bonded with Ir metal and phosphorous atom are described in Patent literatures 7 and 8. However, although they emit blue light, the bond strengths are week so that the heat resistances are extremely poor. Additionally, a complex of which the central metal is bonded with an oxygen atom and a nitrogen atom, is described in Patent literature 9. However, there is no description of any specific advantage of the group bonding to oxygen atom. Further, the complex, of which the central metal bonded with each nitrogen atom being contained in different ring structures, is disclosed in Patent literature 10. Although a device using it exhibits a blue light emission, the external quantum efficiency is low as about 5%.

Patent literature 1: Japanese Patent Application Laid-open No. Heisei 8 (1996)-239655, Patent literature 2: Japanese Patent Application Laid-open No. Heisei 7 (1995)-138561, Patent literature 3: Japanese Patent Application Laid-open No. Heisei 3 (1991)-200889, Patent literature 4: U.S. Pat. No. 6,097,147, Patent literature 5: International PCT publication No. WO01/41512, Patent literature 6: U.S. Patent Application Laid-open No. 2001/0025108, Patent literature 7: U.S. Patent Application Laid-open No. 2002/0182441, Patent literature 8: Japanese Patent Application Laid-open No. 2002-170684, Patent literature 9: Japanese Patent Application Laid-open No. 2003-123982, Patent literature 10: Japanese Patent Application Laid-open No. 2003-133074, Non-patent literature 1: D. F. OBrien and M. A. Baldo et al "Improved energy transfer in electrophosphorescent devices" Vol. 74 No. 3, pp 442-444, Jan. 18, 1999, and Non-patent literature 2: M. A. Baldo et al "Very high-efficiency green organic light-emitting devices based in electrophosphorescence" Applied Physics letters, Vol. 75 No. 1, pp 4-6, Jul. 5, 1999.

DISCLOSURE OF THE INVENTION

The present invention has been made to overcome the above problems and has an objective of providing an organic EL device having a high efficiency of light emission and a long lifetime, and also a novel metal complex compound for producing the organic EL device.

As a result of intensive researches and studies to achieve the above objectives by the present inventors, it was found that employing a metal complex compound represented by the general formula (1) enables to provide an organic electroluminescence device having a great efficiency of light emission and a long lifetime.

Namely, the present invention is:

(a) a metal complex compound represented by the following general formula (1):

wherein M represents a metal atom selected from the group consisting of iridium (Ir), platinum (Pt) and rhodium (Rh), L1 and L2 represent bidentate ligands which are different from each other, the sectional structure $(L_1)_m M$ is represented by the following general formula (2), and the sectional structure $M(L_2)_n$ is represented by the following general formula (3), m and n each represents an integer of 1 or 2, and m+n represents an integer of 2 or 3,

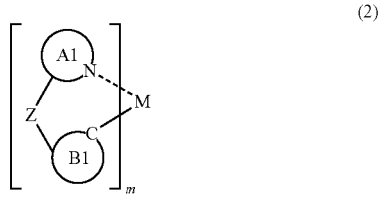

wherein N and C each represents a nitrogen atom and a carbon atom, A1 ring represents a substituted or unsubstituted aromatic heterocyclic group having 3 to 50 ring carbon atoms containing nitrogen atom, B1 ring represents a substituted or unsubstituted aryl group, containing a nitrogen atom, having 6 to 50 ring carbon atoms, and the A1 ring and the B1 ring is inked each other by a covalent bond via Z. Z represents a single bond, —O—, —CO—, —(CR'R")$_a$—, —(SiR'R")$_a$— or —NR'—; wherein R' and R" each independently represents a hydrogen atom, a substituted or unsubstituted aryl group having 6 to 50 ring carbon atoms, a substituted or unsubstituted aromatic heterocyclic group having 3 to 50 ring atoms, or a substituted or unsubstituted alkyl group having 1 to 50 carbon atoms, and a represents an integer of 1 to 10, and R' and R" are the same with or different from each other,

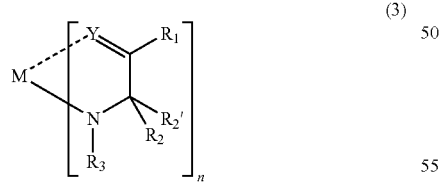

wherein N represents a nitrogen atom, and $R_1$, $R_2$, $R_2$' and $R_3$ each independently represents a substituted or unsubstituted alkyl group having 1 to 50 carbon atoms, a substituted or unsubstituted alkenyl group having 2 to 50 carbon atoms, or a substituted or unsubstituted aryl group having 6 to 50 ring carbon atoms. $R_2$' may be a hydrogen atom. $R_1$ and $R_2$, $R_1$ and $R_2$', $R_2$ and $R_2$', $R_2$ and $R_3$, and $R_2$' and $R_3$ may be inked each other to form a saturated or unsaturated ring structure. Y represents a group represented by an oxygen atom or a sulfur atom, (b) The metal complex compound in (a) in which the sectional structure $M(L_2)_n$ of the general formula (1) is represented by the following general formula (3'):

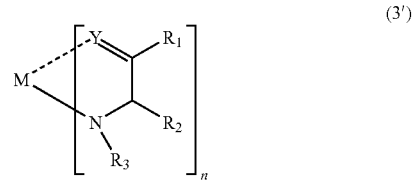

wherein N represents a nitrogen atom, M, Y, $R_1$, $R_2$ and $R_3$ are the same with the aforementioned. $R_1$ and $R_2$, and $R_2$ and $R_3$ may be inked each other to form a saturated or unsaturated ring structure, (c) The metal complex compound in (a) in which the sectional structure $(L_1)_m M$ of the general formula (2) is represented by the general formula (4), (5) or (6):

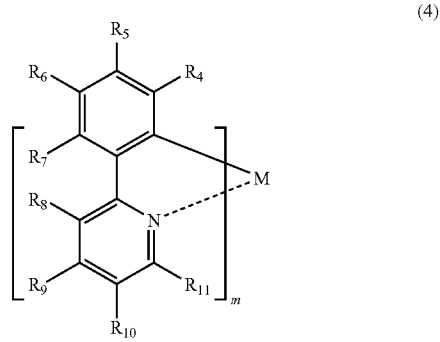

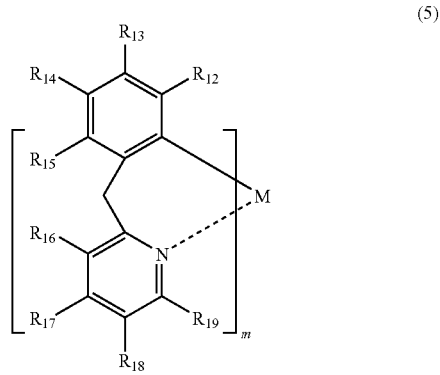

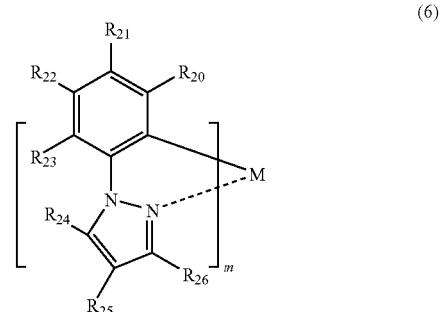

wherein M and m are the same with the aforementioned. $R_4$ to $R_{26}$ each independently represents a hydrogen atom, a substituted or unsubstituted alkyl group having 1 to 30 carbon atoms, a substituted or unsubstituted halogenated alkyl group having 1 to 30 carbon atoms, a substituted or unsubstituted alkoxy group having 1 to 30 carbon atoms, a substituted or unsubstituted heterocyclic group having 3 to 20 ring atoms, a substituted or unsubstituted aryl group having 6 to 40 ring carbon atoms, a substituted or unsubstituted aryloxy group having 6 to 40 ring carbon atoms, a substituted or unsubstituted aralkyl group having 7 to 40 carbon atoms, a substituted or unsubstituted alkenyl group having 2 to 30 carbon atoms, a substituted or unsubstituted arylamino group having 6 to 80 ring carbon atoms, a substituted or unsubstituted alkylamino group having 1 to 60 carbon atoms, a substituted or unsubstituted aralkylamino group having 7 to 80 carbon atoms, a substituted or unsubstituted alkylsilyl group having 1 to 30 carbon atoms, a substituted or unsubstituted arylsilyl group having 6 to 40 carbon atoms, a halogen atom, a cyano group, a nitro group, —S(R)O$_2$, or —S(R)O; wherein R represents a substituent, and neighboring groups among $R_4$ to $R_{11}$, $R_{12}$ to $R_{19}$ and $R_{20}$ to $R_{26}$ may be inked each other to form a saturated or unsaturated ring structure, (d) The metal complex compound of (a), wherein the sectional structure $M(L_2)_n$ represented by the general formula (3) is a sectional structure represented by the following general formula (7):

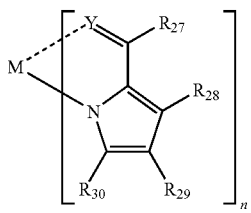

(7)

wherein M, Y and n are the same with aforementioned. $R_{27}$ to $R_{30}$ each independently represents the same with $R_4$ to $R_{26}$ of the aforementioned general formulae (4) to (6). $R_{27}$ and $R_{28}$, $R_{28}$ and $R_{29}$, and $R_{29}$ and $R_{30}$ may be linked each other to form a saturated or unsaturated ring structure, (e) The metal complex compound of (a), wherein the sectional structure $(L_1)_mM$ represented by the above general formula (2) is a sectional structure represented by the above general formula (4), (5) or (6), and the sectional structure $M(L_2)_n$ represented by the above general formula (3) is a sectional structure represented by the above general formula (7), (f) The metal complex compound of (a), wherein the sectional structure $(L_1)_mM$ represented by the above general formula (2) is a sectional structure represented by the above general formula (4), (5) or (6), and the sectional structure $M(L_2)_n$ represented by the above general formula (3) is a sectional structure represented by the following general formula (8), m represents 2, n represents 1 and M represents Ir:

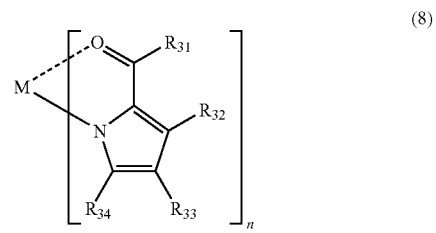

(8)

wherein $R_{31}$ to $R_{34}$ each independently is the same with $R_{27}$ to $R_{30}$ of the above general formula (7), (g) an organic EL device comprising at least any one of organic thin film layers including a light emitting layer between an anode and a cathode, wherein at least any one of the organic thin film layers contains a metal complex compound of (a) to (f), (h) an organic EL device described in (g) wherein said light emitting layer contains the metal complex compound of (a) to (f) as a light emitting material.

(i) an organic EL device described in (g) wherein said light emitting layer contains the metal complex compound of Claim 1 as a dopant.

(j) an organic EL device described in (g) wherein the device comprises at least any one of an electron injecting layer and an electron transporting layer between said light emitting layer and the cathode, and at least any one of the electron injecting layer and the electron transporting layer contains π-electron deficiency nitrogen-containing heterocyclic derivative as the main component, and (k) an organic EL device described in (g) comprising a reductive dopant added into an interface area between a cathode and said organic thin film layer are provided.

The present invention provides an organic EL device having a high efficiency of light emission and a long lifetime, and also a novel metal complex compound for producing the organic EL device.

THE PREFERRED EMBODIMENT TO CARRY OUT THE INVENTION

The metal complex compound of the present invention is represented by the following general formula (1):

(1)

wherein M represents a metal atom selected from the group consisting of iridium (Ir), platinum (Pt) and rhodium (Rh), $L_1$ and $L_2$ represent bidentate ligands which are different from each other, the sectional structure of $(L_1)_mM$ is represented by the following general formula (2), and the sectional structure of $M(L_2)_n$ is represented by the following general formula (3); wherein m and n each represents an integer of 1 or 2, and m+n represents an integer of 2 or 3.

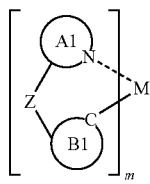

(2)

wherein N and C each represent a nitrogen atom and a carbon atom, A1 ring represents a substituted or unsubstituted nitrogen-containing aromatic heterocyclic group having 3 to 50 carbon ring atoms, and B1 ring represents a substituted or unsubstituted aryl group having 6 to 50 ring carbon atoms.

The nitrogen-containing aromatic heterocyclic group includes preferably the group having 3 to 20 ring atoms, more preferably the group having 3 to 10 ring atoms. Examples of the nitrogen-containing aromatic heterocyclic group include pyrazinyl group, pyridyl group, pyrimidinyl group, pyrazolyl group, imidazolyl group, indo idinyl group, imidazopyridinyl group, quinolyl group, isoquinolyl group, quinoxalinyl group and the like.

Among those, pyrazinyl group, pyridyl group, pyrimidinyl group, pyrazolyl group, imidazolyl group, quinolyl group and isoquinolyl are preferable.

The aryl group of the above B1 ring includes preferably the group having 6 to 50 ring carbon atoms, more preferably the group having 6 to 24 ring carbon atoms. The aryl group includes phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenyl-yl group, 4"-t-butyl-p-terphenyl-4-yl group, o-cumenyl group, m-cumenyl group, p-cumenyl group, 2,3-xylyl group, 3,4-xylyl group, 2,5-xylyl group, mesityl group and the like.

Among those, phenyl group, 1-naphthyl group, 2-naphthyl group, 9-phenanthryl group, 2-biphenylyl group, 3-biphenylyl group, 4-biphenylyl group, p-tolyl group and 3,4-xylyl group are preferable.

In the general formula (2), A1 ring and B1 ring is inked each other by a covalent bond via Z. Z represents a single bond, —O—, —S—, —CO—, —(CR'R")$_a$—, —(SiR'R")$_a$— or —NR'—, wherein R' and R" each independently represents a hydrogen atom, a substituted or unsubstituted aryl group having 6 to 50 ring carbon atoms, a substituted or unsubstituted aromatic heterocyclic group having 3 to 50 ring atoms, or a substituted or unsubstituted alkyl group having 1 to 50 carbon atoms, a represents an integer of from 1 to 10, and R' and R" are the same with or different from each other.

Examples of an aryl group represented by R' and R" include the similar ones mentioned in the above B1 ring, and examples of the aromatic heterocyclic group include the similar ones mentioned in the above A1 ring.

Substituted or unsubstituted alkyl group having 1 to 50 carbon atoms includes preferably the group having 1 to 10 carbon atoms. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoethyl group, 2,3-dicyano-t-butyl group, 1,2,3-tricyanopropyl group, nitromethyl group, 1-nitroethyl group, 2-nitroethyl group, 1,2-nitroethyl group, 2,3-dinitro-t-butyl group, 1,2,3-trinitropropyl group, cyclopentyl group, cyclohexyl group, cyclooctyl group, 3,5-dimethylcyclohexyl group, 3,3,5,5-tetramethylcyclohexyl group and the like.

Among those, methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 1-pentylhexyl group, 1-butylpentyl group, 1-heptyloctyl group, cyclohexyl group, cyclooctyl group, 3,5-dimethylcyclohexyl group, and 3,3,5,5-tetramethylcyclohexyl group are preferable.

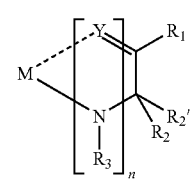

(3)

In the general formula (3), N represents a nitrogen atom, and $R_1$, $R_2$, $R_2'$ and $R_3$ each independently represents a substituted or unsubstituted alkyl group having 1 to 50 carbon atoms, a substituted or unsubstituted alkenyl group having 2 to 50 carbon atoms, or a substituted or unsubstituted aryl group having 6 to 50 ring carbon atoms. $R_2'$ may be a hydrogen atom. $R_1$ and $R_2$, $R_1$ and $R_2'$, $R_2$ and $R_2'$, $R_2$ and $R_3$, and $R_2'$ and $R_3$ may be linked each other to form a saturated or unsaturated ring structure. Y represents a group represented by an oxygen atom or a sulfur atom.

The metal complex compound of the present invention is the compound which the sectional structure $M(L_2)_n$ of the above general formula (1) is represented by the following general formula (3'):

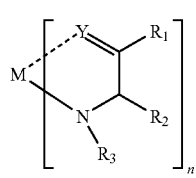

(3')

wherein N represents a nitrogen atom, M, Y, $R_1$, $R_2$ and $R_3$ are the same with the aforementioned. $R_1$ and $R_2$, and $R_2$ and $R_3$ may be inked each other to form a saturated or unsaturated ring structure.

Examples of a substituted or unsubstituted alkyl group having 1 to 50 carbon atoms for $R_1$, $R_2$, $R_2'$ and $R_3$ include the similar ones to the examples of R' and R" mentioned in the above Z. Examples of a substituted or unsubstituted aryl group having 6 to 50 ring carbon atoms for $R_1$, $R_2$, $R_2'$ and $R_3$ include perfluorophenyl group as well as the examples mentioned for the above B1 ring, and also preferable ones are the similar ones as well.

An alkenyl group having 2 to 50 carbon atoms for $R_1$, $R_2$, $R_2'$ and $R_3$ includes the group having 2 to 16 carbon atoms preferably. Examples of the alkenyl group include vinyl group, allyl group, 1-butenyl group, 2-butenyl group, 3-butenyl group, 1,3-butanedienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl-1-butenyl group, 3-phenyl-1-butenyl group and the like. Styryl group, 2,2-diphenylvinyl group and 1,2-diphenylvinyl group are preferable.

In the general formula (3), $R_1$ and $R_2$, $R_1$ and $R_2'$, $R_2$ and $R_2'$, $R_2$ and $R_3$, and $R_2'$ and $R_3$ may be inked each other to form a saturated or unsaturated ring structure. In addition, $R_1$ and $R_2$, and $R_2$ and $R_3$ in the general formula (3') may be linked each other to form a saturated or unsaturated ring structure.

The saturated or unsaturated ring structures formed by bonding each other include, for example, a cycloalkane having 4 to 12 carbon atoms such as cyclobutane, cyclopentane, cyclohexane, adamantane and norbornane, a cycloalkene having 4 to 12 carbon atoms such as cyclobutene, cyclopentene, cyclohexene, cycloheptene and cyclooctene, a cycloalkadiene having 6 to 12 carbon atoms such as cyclohexadiene, cycloheptadiene and cyclooctadiene, an aromatic ring having 6 to 50 carbon atoms such as benzene, naphthalene, phenanthrene, anthracene, pyrene, chrysene and acenaphthylene and the like.

The metal complex compound of the general formula (1) of the present invention is the compound which the sectional structure $(L_1)_m M$ of the above general formula (2) is represented by the following general formula (4), (5) or (6):

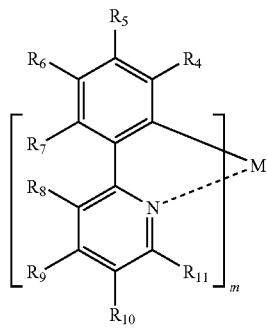

(4)

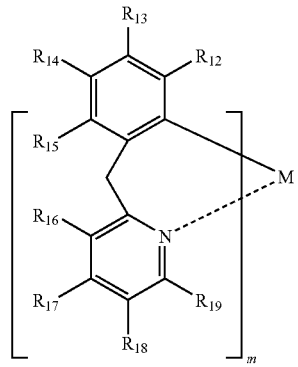

(5)

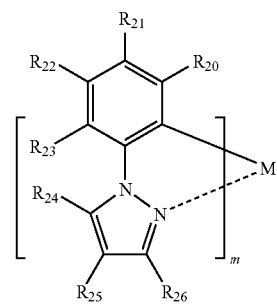

(6)

M and n in the general formulae (4), (5) and (6) are the same with aforementioned. $R_4$ to $R_{26}$ each independently includes hydrogen atom, a substituted or unsubstituted alkyl group having 1 to 30 carbon atoms, a substituted or unsubstituted halogenated alkyl group having 1 to 30 carbon atoms, a substituted or unsubstituted alkoxy group having 1 to 30 carbon atoms, a substituted or unsubstituted heterocyclic group having 3 to 20 ring atoms, a substituted or unsubstituted aryl group having 6 to 40 ring carbon atoms, a substituted or unsubstituted aryloxy group having 6 to 40 ring carbon atoms, a substituted or unsubstituted aralkyl group having 7 to 40 carbon atoms, a substituted or unsubstituted alkenyl group having 2 to 30 carbon atoms, a substituted or unsubstituted arylamino group having 6 to 80 carbon atoms, a substituted or unsubstituted alkylamino group having 1 to 60 carbon atoms, a substituted or unsubstituted aralkylamino group having 7 to 80 carbon atoms, a substituted or unsubstituted alkylsilyl group having 1 to 30 carbon atoms, a substituted or unsubstituted arylsilyl group having 6 to 40 carbon atoms, a halogen atom, a cyano group, a nitro group, —S(R)$O_2$, or —S(R)O; wherein R represents a substituent.

Examples of the substituted or unsubstituted alkyl group having 1 to 30 carbon atoms, the substituted or unsubstituted aryl group having 6 to 40 ring carbon atoms and the substituted or unsubstituted alkenyl group having 2 to 30 carbon atoms include the similar groups to aforementioned.

The substituted or unsubstituted halogenated alkyl group having 1 to 30 carbon atoms is preferably the group having 1 to 10 carbon atoms. Examples of the halogenated alkyl group include chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoisobutyl group, 1,2-diiodoethyl group, 1,3-diiodoisopropyl group, 2,3-diiodo-t-butyl group, 1,2,3-triiodopropyl group, fluoromethyl group, 1 fluoroethyl group, 2-fluoromyl group, 2-fluoroisobutyl group, 1,2-difluoroethyl group, difluoromethyl group, trifluoromethyl group, pentafluoroethyl group, perfluoroisopropyl group, perfluorobutyl group, perfluorocyclohexyl group, and the like.

Among those, fluoromethyl group, trifluoromethyl group, pentafluoroethyl group, perfluoroisopropyl group, perfluorobutyl group and perfluorocyclohexyl group are preferable.

The substituted or unsubstituted al oxy group having 1 to 30 carbon atoms is represented by —OX$_1$, and examples of X$_1$ include the similar groups to those mentioned in the alkyl group and the halogenated alkyl group above.

The substituted of unsubstituted heterocyclic group having 3 to 20 ring carbon atoms includes preferably the group having 3 to 10 ring carbon atoms. Specific examples thereof include 1-pyrrolyl group, 2-pyrrolyl group, 3-pyrrolyl group, pyradinyl group, 2-pyridinyl group, 1-imidazolyl group, 2-imidazolyl group, 1-pyrazolyl group, 1-indolyzinyl group, 2-indolyzinyl group, 3-indolyzinyl group, 5-indolyzinyl group, 6-indolyzinyl group, 7-indolyzinyl group 8-indolyzinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 9-carbazolyl group, β-carboline-1-yl group, β-carboline-3-yl group, β-carboline-4-yl group, β-carboline-5-yl group, β-carboline-6-yl group, β-carboline-7-yl group β-carboline-8-yl group, β-carboline-9-yl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10)-phenanthrolin-3-yl group 1,10-phenanthrolin-4-yl group, 1,10-phenanthrolin-5-yl group, 2,9-phenanthrolin-1-yl group, 2,9-phenanthrolin-1-yl group, 2,9-phenanthrolin-4-yl group, 2,9-phenanthrolin-5-yl group, 2,9-phenanthrolin-6- yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-yl group, 2,8-phenanthrolin-6-yl group, 2,8-phenanthrolin-7-yl group, 2,8-phenanthrolin-9-yl group, 2,8-phenanthrolin-O-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-O-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrol-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl 1-indolyl group, 4-t-butyl 1-indolyl group, 2-t-butyl 3-indolyl group, 4-t-butyl 3-indolyl group and the like.

Among those, 2-pyridinyl group, 1-indolyzinyl group, 2-indolyzinyl group, 3-indolyzinyl group, 5-indolyzinyl group, 6-indolyzinyl group, 7-indolyzinyl group, 8-indolyzinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 1-carbazolyl group, 2-carbazolyl group, 3-carbazolyl group, 4-carbazolyl group and 9-carbazolyl group are preferable.

The substituted or unsubstituted aryloxy group having 6 to 40 ring atoms is represented by —OAr, and examples of Ar include the similar groups to those mentioned in the aryl group.

The substituted or unsubstituted aralkyl group having 7 to 40 carbon atoms is preferably the group having 7 to 18 carbon atoms. Examples of the aralkyl group include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group and the like. Benzyl group, p-cyanobenzyl group, m-cyanobenzyl group, o-cyanobenzyl group, 1-phenylethyl group, 2-phenylethyl group, 1-phenylisopropyl group and 2-phenylisopropyl group are preferable.

The substituted or unsubstituted arylamino group having 6 to 80 ring carbon atoms, the substituted or unsubstituted aylamino group having 1 to 60 carbon atoms and the substituted or unsubstituted aralkylamino group having 7 to 80 carbon atoms are represented by $-NQ_1Q_1$. $Q_1$ and $Q_2$ each independently is preferably the groups having 1 to 20 carbon atoms, and a hydrogen atom and the similar examples to those mentioned in the aryl group, the alkyl group and the aralkyl group are mentioned.

The substituted or unsubstituted alkylsilyl group having 1 to 30 carbon atoms includes trimethylsilyl group, triethylsilyl group, t-butyldimethylsilyl group, vinyldimethylsilyl group, propyldimethylsilyl and the like.

The substituted or unsubstituted alkylsilyl group having 6 to 40 carbon atoms includes triphenylsilyl group, phenyldimethylsilyl group; t-butyldiphenylsilyl group and the like.

The halogen atom includes, for example, fluorine, chlorine, bromine, iodine and the like. The substituent R of $-S(R)O_2$ and $-S(R)O$ includes the similar groups to those of the above $R_4$ to $R_{26}$. In the general formulae (4), (5) and (6), neighboring groups among $R_4$ to $R_{11}$, $R_{12}$ to $R_{19}$ and $R_{20}$ to $R_{26}$ may be linked each other to form a saturated or unsaturated ring structure. The ring structures include the similar structures to aforementioned.

The metal complex compound of the general formula (1) of the present invention is the compound which the sectional structure $M(L_2)_n$ of the above general formula (3) is represented by the following general formula (7):

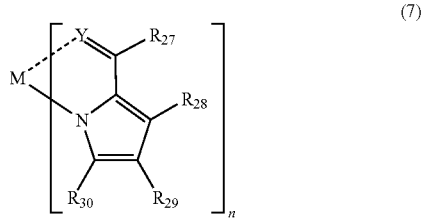

(7)

M, Y and n in the general formulae (7) are the same with the aforementioned. $R_{27}$ to $R_{30}$ each independently is the same with $R_4$ to $R_{26}$ in the above general for formulae (4) to (6) $R_{27}$ and $R_{28}$, $R_{28}$ and $R_{29}$, and $R_{29}$ and $R_{30}$ each independently may be inked each other to form a saturated or unsaturated ring structure.

The metal complex compounds represented by the general formula (1) of the present invention comprise the sectional structure $(L_1)_mM$ of the above general formula (2) which is represented by the above general formula (4), (5) or (6), and the sectional structure $M(L_2)_n$ of the above general formula (3) which is represented by the above general formula (7).

The metal complex compounds represented by the general formula (1) of the present invention comprise the sectional structure $(L_1)_mM$ of the above general formula (2) which is represented by the above general formula (4), (5) or (6), and the sectional structure $M(L_2)_n$ of the above general formula (3) which is represented by the above general formula (8), in which m represents 2, n represents 1 and M represents Ir.

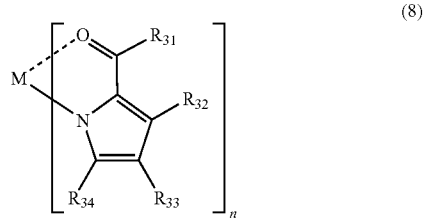

(8)

$R_{31}$ to $R_{34}$ in the general formula (8) each independently is the same with $R_{27}$ to $R_{30}$ in the above general formula (7).

The organic EL device of the present invention is an organic EL device comprising at least any one of organic thin film layers containing at least any one of a light emitting layers between an anode and a cathode, wherein at least any one of the layers of the organic thin film layers comprises a metal complex compound having any one of the chemical structures or of the sectional structures of the general formulae (1) to (8).

The organic EL device of the present invention comprises the above light emitting layer containing any one of the above metal complex compounds as a light emitting material.

The organic EL device of the present invention comprises the above light emitting layer containing any one of the above metal complex compounds as a dopant.

The organic EL device of the present invention comprises at least any one of an electron injecting layer and an electron transporting layer between the light emitting layer and a cathode and at least any one of the electron injecting layer and the electron transporting layer contains a n-electron deficiency nitrogen-containing heterocyclic derivative as the main component.

The organic EL device of the present invention is the device comprising a reductive dopant added into an interface area between a cathode and the above organic thin film layer.

Examples of the metal complex compound represented by the general formula (1) of the present invention will be shown as follows which do not limit the scope of it. Here, Me represents a methyl group.

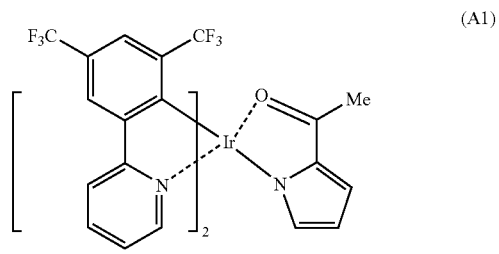

(A1)

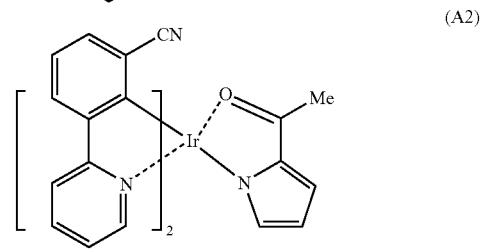

(A2)

-continued
(A3) 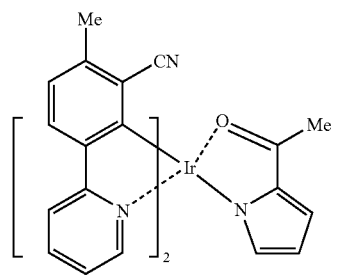
(A4) 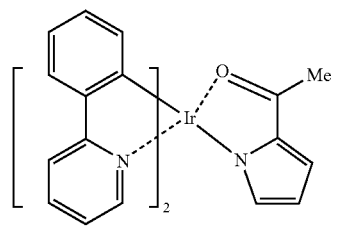
(A5) 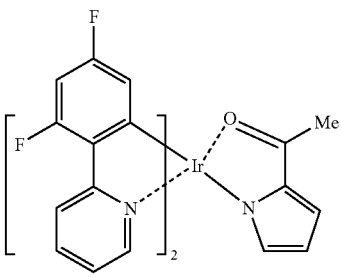
(A6) 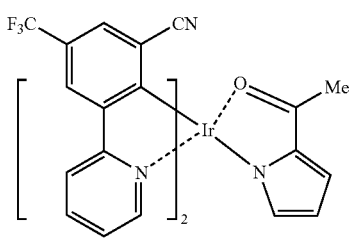
(A7) 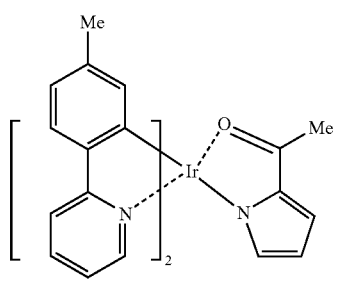
(A8) 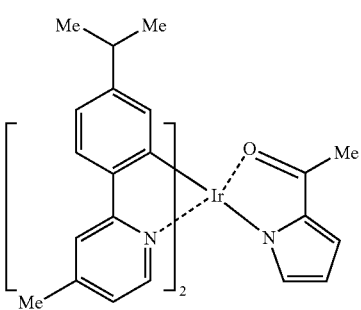
-continued
(A9) 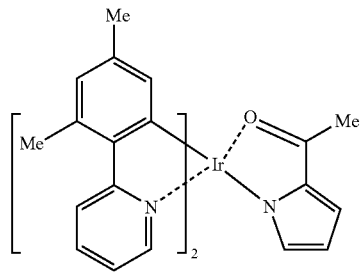
(A10) 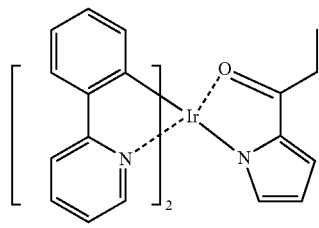
(A11) 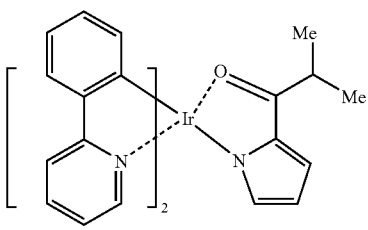
(A12) 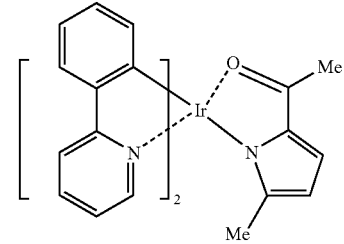
(A13) 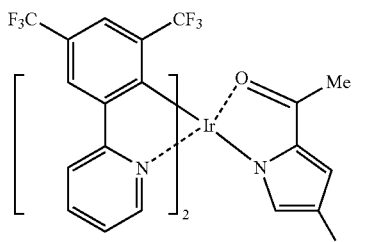
(A14) 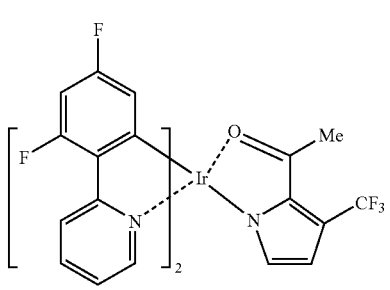

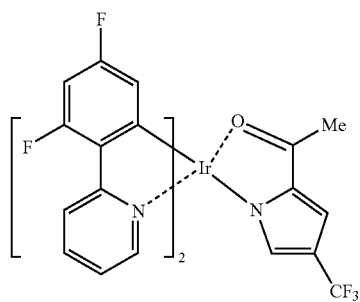
(A15)
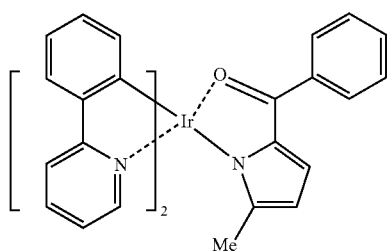
(A16)
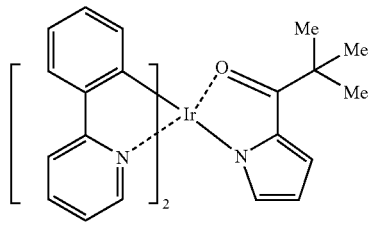
(A17)
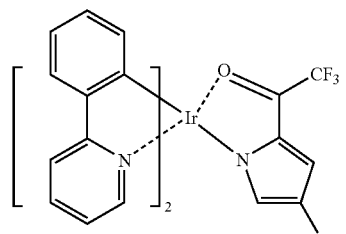
(A18)
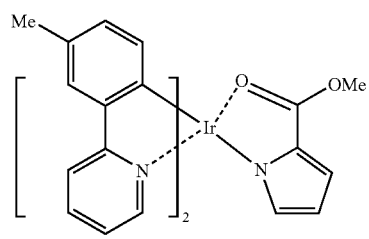
(A19)
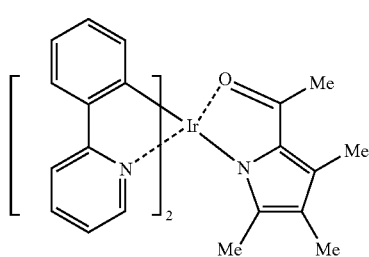
(A20)
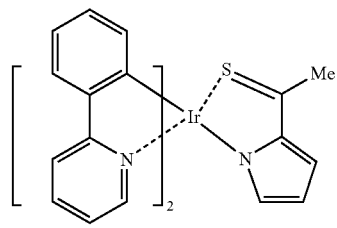
(A21)
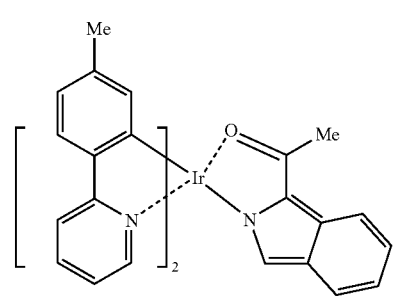
(A22)
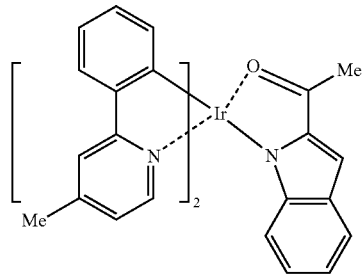
(A23)
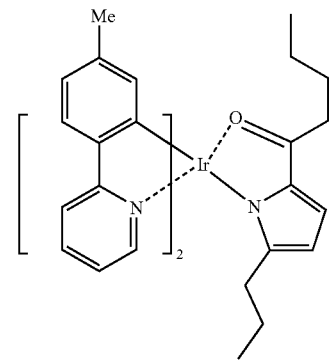
(A24)
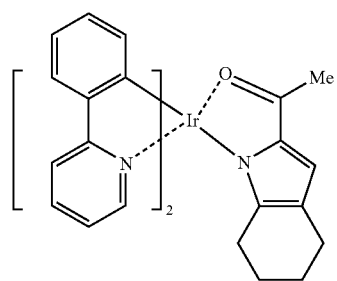
(A25)

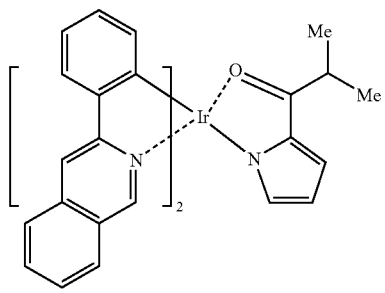
(A26)
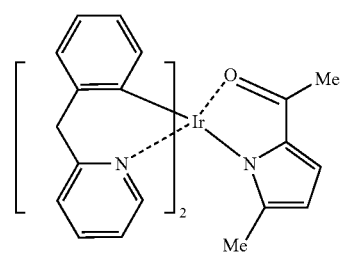
(A28)
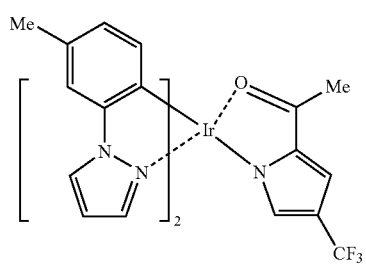
(A29)
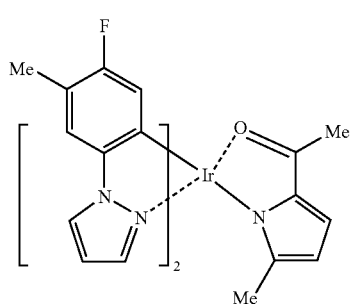
(A30)
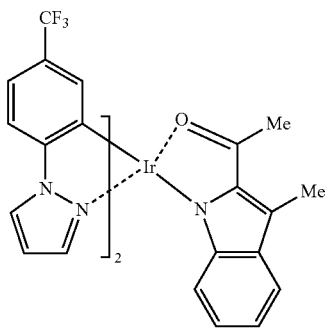
(A31)
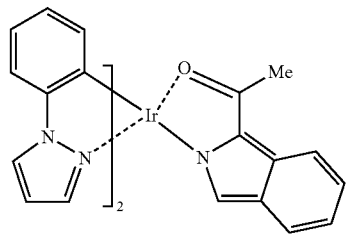
(A32)
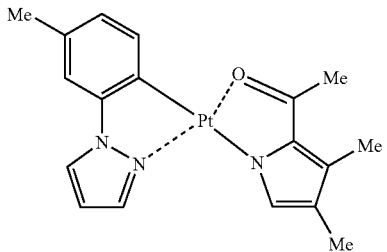
(A33)
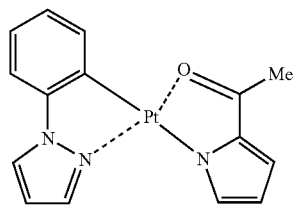
(A34)
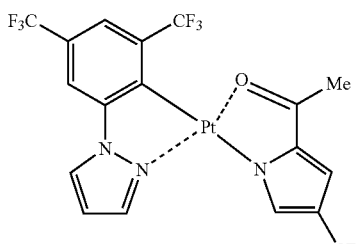
(A35)
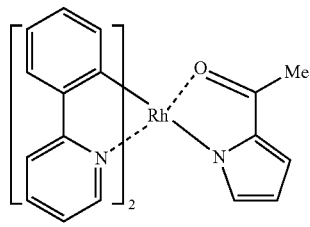
(A36)

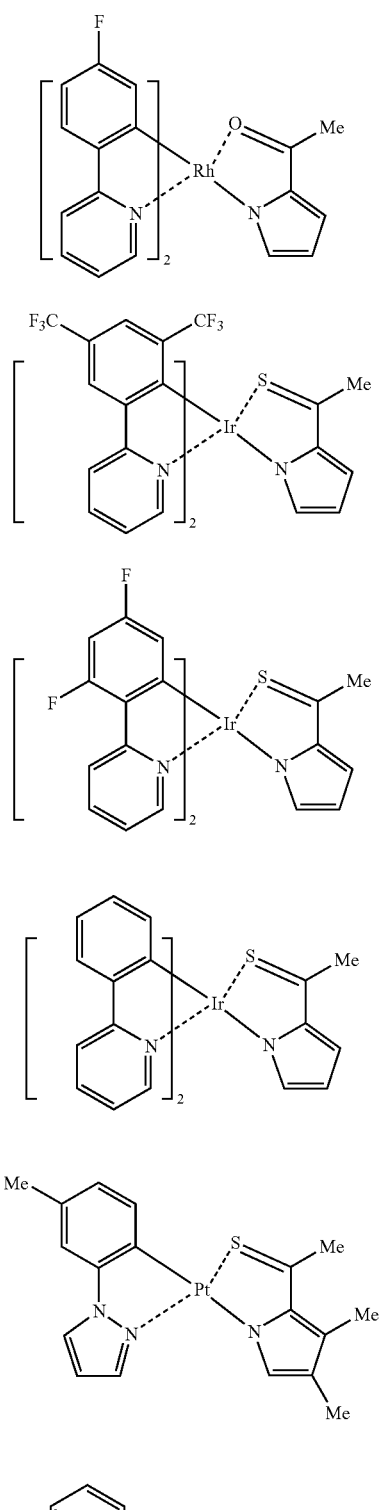

The organic EL device of the present invention is the device comprising at least one of the organic thin film layers containing at least any one of a light emitting layers between an anode and a cathode, wherein at least any one of the layers of the organic thin film layers comprises a metal complex compound of the present invention.

The content of a metal complex compound of the present invention in the above organic thin film layer is generally in the range of from 0.1 to 100% by weight, preferably 1 to 30% by weight in the total weight of the light emitting layer.

In the organic EL device of the present invention, it is preferable that the light emitting layer comprises a metal complex compound of the present invention as the light emitting material. In general, the light emitting layer is formed as a thin layer in accordance with the vacuum vapor deposition process or the coating process. It is preferable that the layer comprising the metal complex compound of the present invention is formed as a thin layer in accordance with the coating process since the production process can be simplified by using the coating process.

In the organic EL device of the present invention, an organic thin film layer, which is a monolayer type, is a light emitting layer, and the light emitting layer contains a metal complex compound of the present invention. Additionally, an organic EL device of a multilayer type includes "an anode/a hole injecting layer (a hole transporting layer)/a light emitting layer/a cathode", "an anode/a light emitting layer/an electron injecting layer (an electron transporting layer)/a cathode", "an anode/a hole injecting layer (a hole transporting layer)/a light emitting layer/an electron injecting layer (an electron transporting layer)/a cathode, and the like.

It is effective for the anode of the organic EL device of the present invention to have a work function of 4.5 eV or larger as it has a role of supplying holes into a hole injecting layer, a hole transporting layer, a light emitting layer and the like. Materials for the anode include metal, alloy, metal oxide, a conductive material or a mixture thereof. Specific examples of the material for the anode include a conductive metal oxide such as tin oxide, zinc oxide, indium oxide and indium tin oxide (ITO), a metal such as gold, silver, chromium and nickel, a mixture or lamination of the conductive material and the metals, an inorganic conductive metal oxide such as copper iodide and copper sulfide, an organic conductive metal oxide such as polyaniline, polythiophene and polypyrrole, and lamination of ITO and those materials. It is preferable to employ the conductive metal oxides, and more preferable to employ ITO) due to its productivity, higher conductivity transparency and the like. It is possible to select a film thickness of the anode appropriately depending on a kind of the materials.

The cathode of the organic EL device of the present invention has a role of supplying electron into an electron injecting layer, an electron transporting layer, a light emitting layer and the like. Materials for the cathode include metal, alloy, metal halide, metal oxide, a conductive compound or a mixture thereof. Specific examples of the material for the cathode include an alkaline metal such as Li, Na and K, fluoride or oxide thereof, an alkaline earth metal such as Mg and Ca, fluoride or oxide thereof, gold, silver, zinc, aluminum, sodium-potassium alloy or mixed metal, lithium-aluminum alloy or mixed metal, magnesium-silver alloy or mixed metal, or rare earth metal such as indium and ytterbium. Among those, aluminum, lithium-aluminum alloy or mixed metal, magnesium-silver alloy or mixed metal, and the like are preferable. The cathode may be a monolayer structure of the aforementioned materials or a layered structure containing those materials. For example, the layered structures of aluminum/lithium fluoride and aluminum/lithium oxide are preferable. It is possible to select a thickness of the cathode appropriately depending on a kind of the materials.

It is possible to use the hole injecting layer and the hole transporting layer of the organic EL device when they have a role of injecting holes from the anode, transporting holes from the anode or blocking electrons injected from the cathode. Specific examples thereof include a carbazol derivative, a triazole derivative, an oxazole derivative, an imidazole derivative, a polyarylalkane derivative, a pyrazoline derivative, a pyrazolon derivative, a phenylenediamine derivative, an arylamine derivative, an amino-substituted chalcone derivative, a stylylanthracene derivative, a fluorenone derivative, a hydrazone derivative, a stilbene derivative, a silazane derivative, an aromatic tertiary-amine compound, a stylylamine compound, an aromatic dimethylidyne-based compound, a porphyrin-based compound, a polysilane-based compound, poly(N-vinylcarbazol) derivative, an aniline-based copolymer, conductive polymeric oligomer such as a thiophene oligomer and polythiophene, an organic silane derivative, the metal complex compounds of the present invention and the like. In addition, the aforementioned hole injecting layer and the aforementioned hole transporting layer may be a monolayer structure comprising at least one or more material of the aforementioned materials or a multilayered structure comprising a plural layer of the same composition or the different composition thereof.

It is possible to use the electron injecting layer and the electron transporting layer of the organic EL device when they have a role of injecting electrons from the cathode, transporting the electrons, or blocking holes injected from the anode. Specific examples thereof include a triazole derivative, an oxazole derivative, an oxadiazole derivative, an imidazole derivative, a fluorenone derivative, an anthraquinodimetane derivative, an anthrone derivative, a diphenylquinone derivative, a thiopyrandioxide derivative, a carbodiimide derivative, a fluorenylidene methane derivative, a distyrylpyradine derivative, an aromatic tetracarboxylic acid anhydride of naphthalene or perylene, a phthalocyanine derivative, a metal complex of a 8-quinolinol derivative, a metal complex represented by the metal complex coordinated with metal phthalocyanine, benzoxazole or benzothiazole, an organic silane derivative, a metal complex compound of the present invention and the like. In addition, the aforementioned electron injecting layer and the aforementioned electron transporting layer may be a monolayer structure comprising at least one or more material of the aforementioned materials or a multilayered structure comprising a plural layer of the same composition or the different composition thereof.

Further, en electron transporting material for the electron injecting layer and the electron transporting layer includes the following compounds:

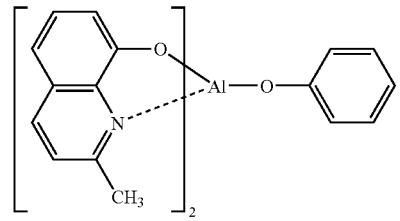
(A-1)

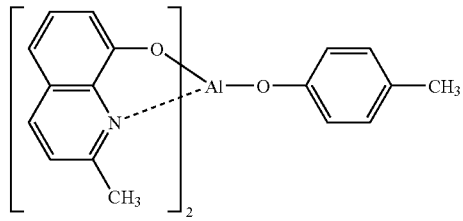
(A-2)

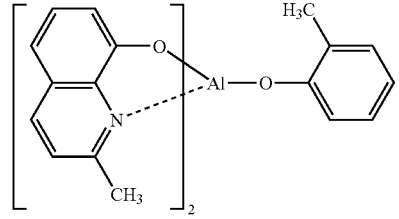
(A-3)

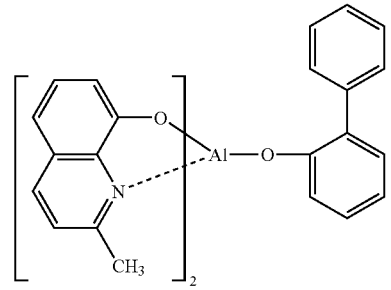
(A-4)

(A-5)
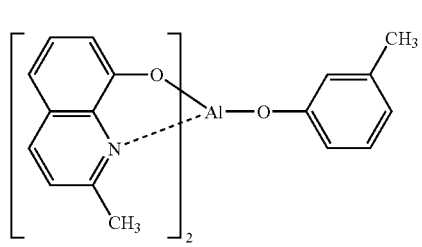
(A-6)
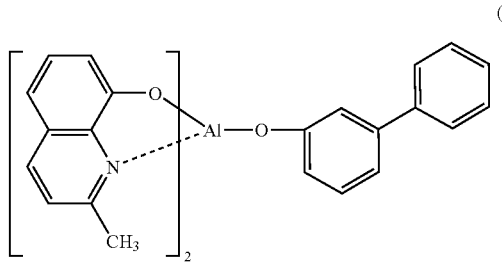
(A-7)
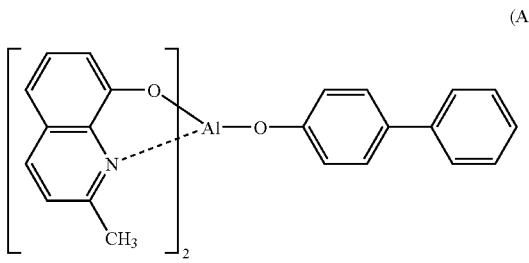
(A-8)
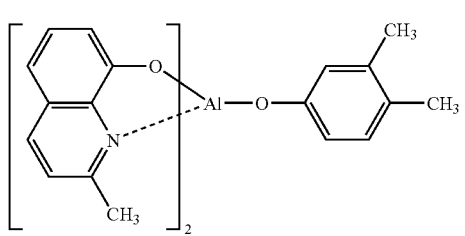
(A-9)
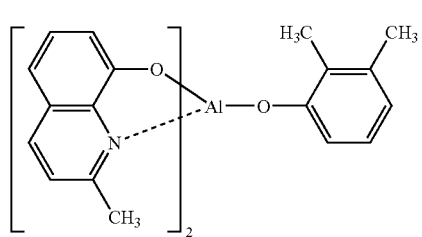
(A-10)
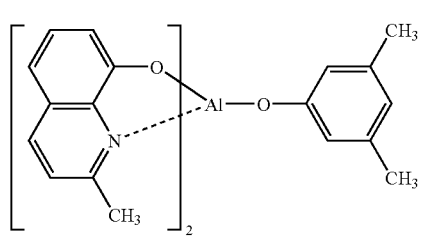
(A-11)
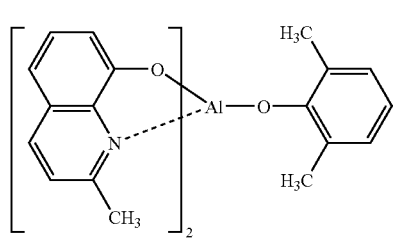
(A-12)
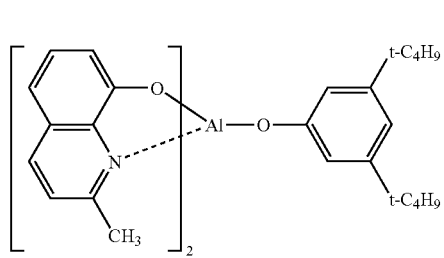
(A-13)
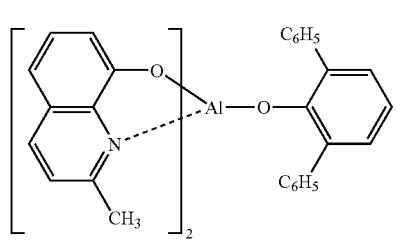
(A-14)
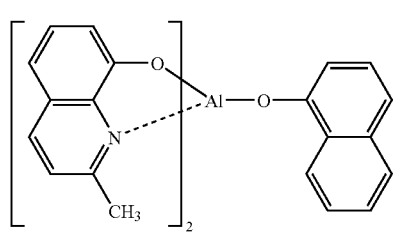
(A-15)
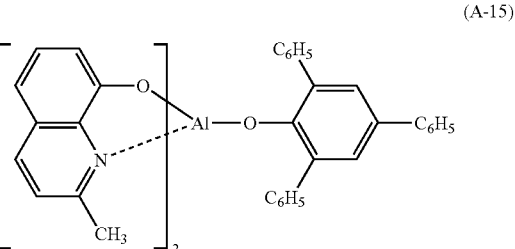
(A-16)
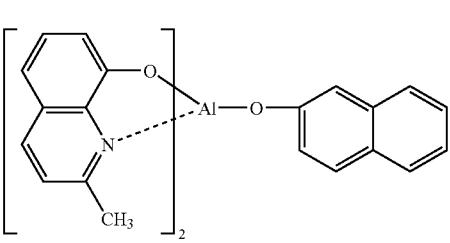

-continued
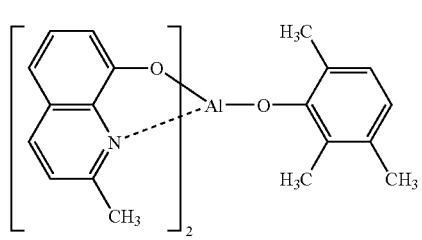
(A-17)
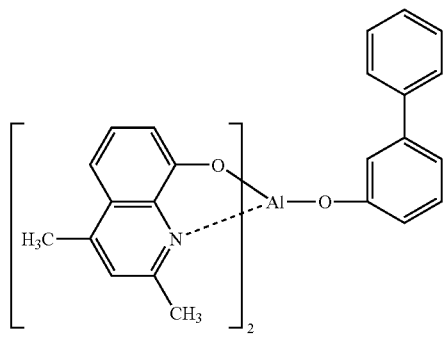
(A-18)
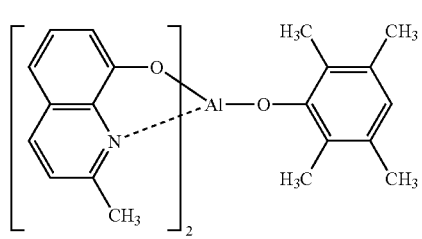
(A-19)
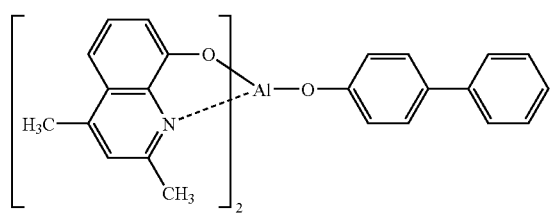
(A-20)
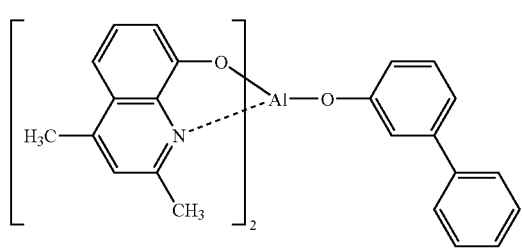
(A-21)
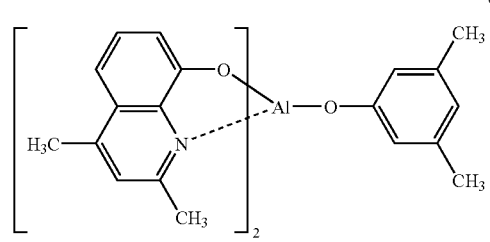
(A-22)
-continued
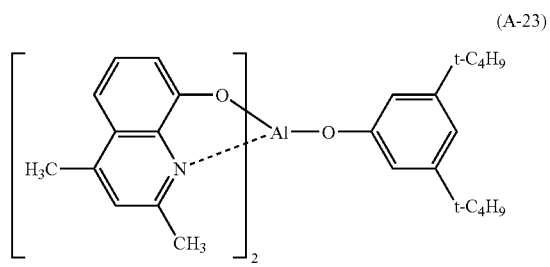
(A-23)
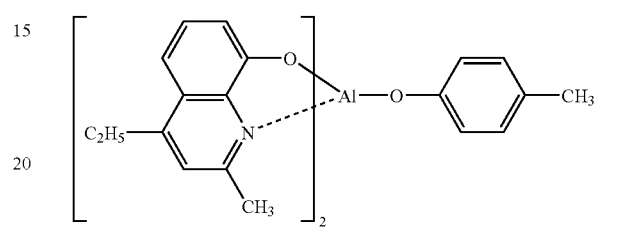
(A-24)
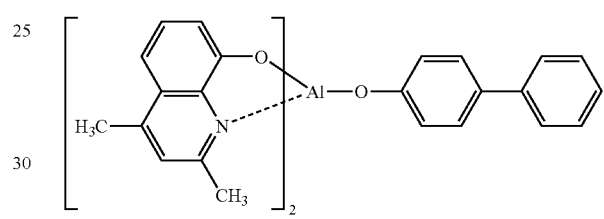
(A-25)
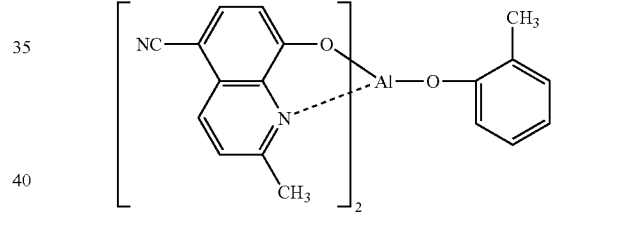
(A-26)
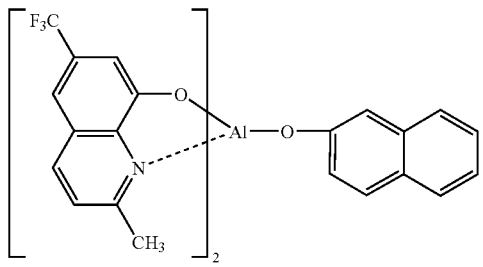
(A-27)
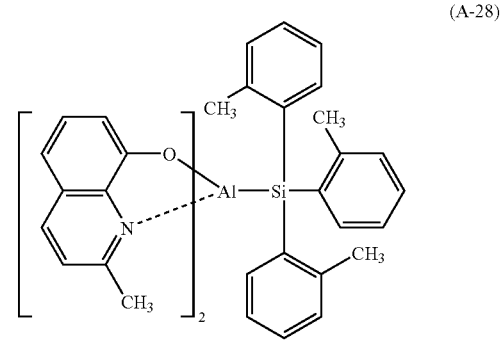
(A-28)

-continued (A-29)
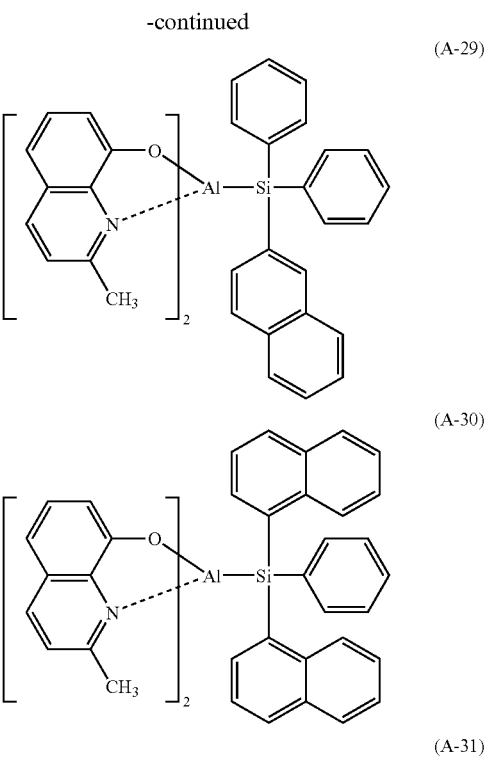

(A-30)

(A-31)
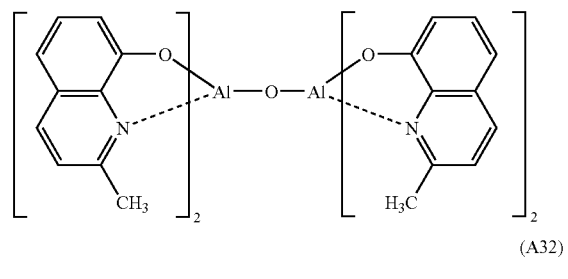

(A32)
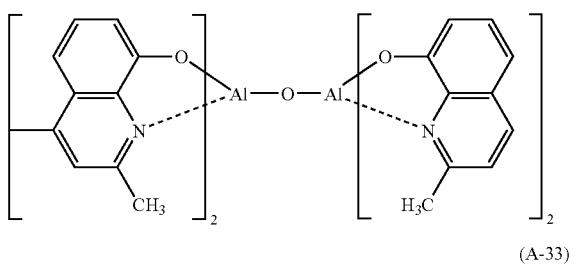

(A-33)
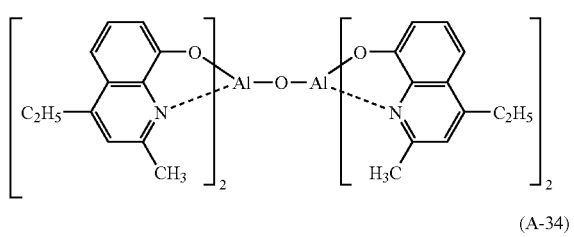

(A-34)
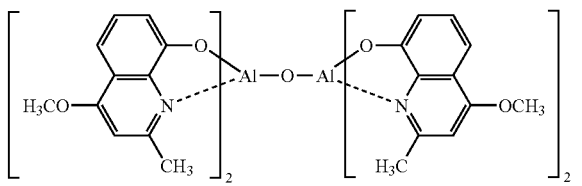

-continued (A-35)

(A-36)
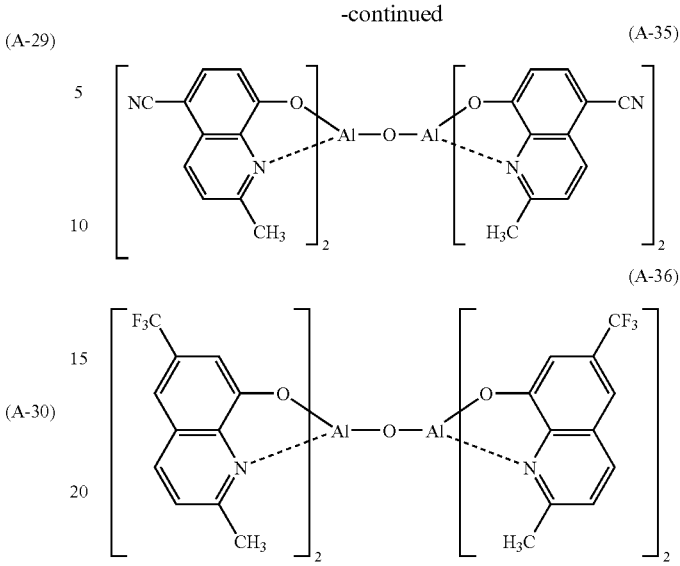

It is preferable in the organic EL device that at least any one of the electron injecting layer and the electron transporting layer contains π-electron deficiency nitrogen-containing heterocyclic derivative as the main component. Examples of the n-electron deficiency nitrogen-containing heterocyclic derivative include preferably a nitrogen-containing 5-members ring derivative such as a benzimidazole ring, a benztriazole ring, a pyridinoimidazole ring, a pyrimidinoimidazole ring and a pyridazinoimidazole ring, and a nitrogen-containing 6 members ring derivative such as a pyridine ring, a pyrimidine ring, a pyrazine ring and a triazine ring. A structure represented by the following general formula B-I is preferable for the nitrogen-containing 5-members ring derivative, and a structure represented by the following general formulae C-I, C-II, C-III, C-VI, C-V and C-VI is preferable for the nitrogen-containing 6-members ring derivative, in particular, the structure represented the general formulae C-I and C-II are is more preferable.

(B-I)
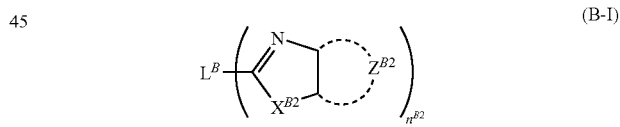

In the general formula (B-I), $L^B$ represents a connecting group having bivalent or more, and a connecting group formed by carbon, si icon, nitrogen, boron, oxygen, sulfur, metal, metal ion or the like is preferable, and a carbon atom a nitrogen atom, a silicone atom, a boron atom, an oxygen atom, a sulfur atom, an aromatic hydrocarbon ring and an aromatic heterocyclic ring are more preferable, a carbon atom, a silicon atom, an aromatic hydrocarbon ring and an aromatic heterocyclic ring are particularly preferable.

$L^B$ may have a substituent, and a preferable substituent includes an alkyl group, an alkenyl group, an alkynyl group, an aromatic hydrocarbon group, an amino group, an alkoxy group, an aryloxy group, an acyl group, an al oxycarbonyl group, an aryloxycarbonyl group, an acyloxy group, an acylamino group, an alkoxycarbonylamino group, an aryloxycarbonylamino group, a sulfonylamino group a sulfamoyl group, a carbamoyl group, an alkylthio group an arylthio group a sulfonyl group, a halogen atom, a cyano group and an aromatic heterocyclic group. More preferable one includes an alkyl group, an aryl group, an alkoxy group, an aryloxy group, a halogen atom, an cyano group and an aromatic heterocyclic group, and further more preferable one includes an alkyl group, an aryl group, an alkoxy group, an aryloxy group and an aromatic heterocyclic group, particularly preferable one includes an alkyl group, an aryl group and an aromatic heterocyclic group.

Examples of the connecting group represented by $L^B$ include the following:

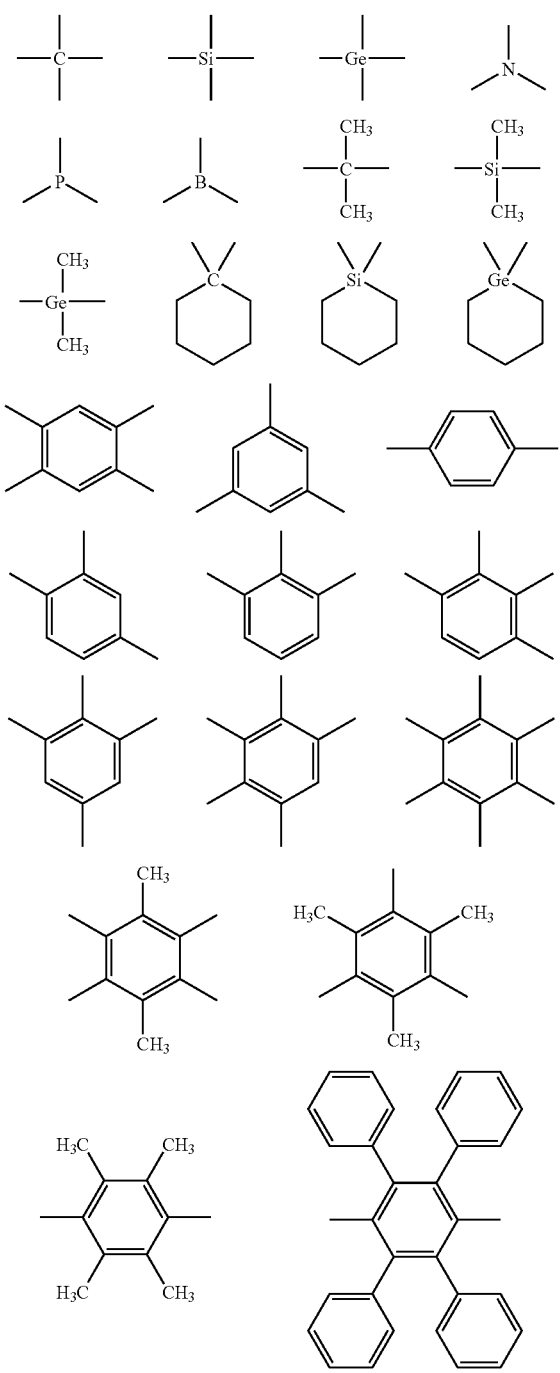

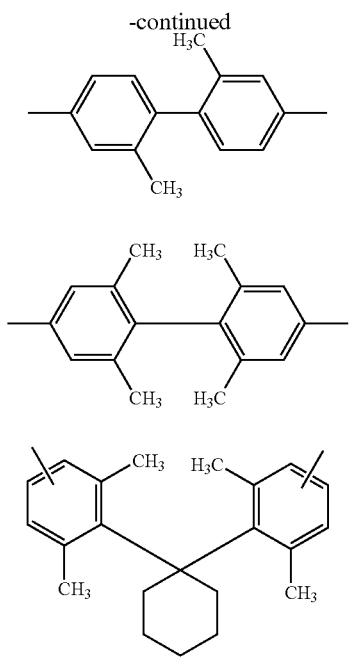

In the general formula (B-I), $X^{B2}$ represents —O—, —S— or =N—$R^{B2}$. $R^{B2}$ represents a hydrogen atom, an aliphatic hydrocarbon group, an aryl group and a heterocyclic group.

An aliphatic hydrocarbon group represented by $R^{B2}$ includes a linear, branched or cyclic alkyl group having preferably 1 to 20 carbon atoms, more preferably 1 to 12 carbon atoms and in particular preferably 1 to 8 carbon atoms. Specific examples include methyl, ethyl isopropyl, t-butyl, n-octyl, n-decyl, n-hexadecyl, cyclopropyl, cyclopentyl, cyclohexyl and the like. An alkenyl group thereof includes the group having preferably 2 to 20 carbon atoms, more preferably 2 to 12 carbon atoms, in particular preferably 2 to 8 carbon atoms. Specific examples include a vinyl group, an aryl group, 2-butenyl group, 3-pentenyl group and the like. An ynyl group thereof includes the group having preferably 2 to 20 carbon atoms, more preferably 2 to 12 carbon atoms, in particular preferably 2 to 8 carbon atoms. Specific examples thereof include a propargyl group, a 3-pentyl group and the like. An alkyl group is more preferable.

An aryl group represented by $R^{B2}$ include a monocyclic or a condensed cyclic aryl group having preferably 6 to 30 carbon atoms, more preferably 6 to 20 carbon atoms, and further more preferably 6 to 12 carbon atoms. Specific examples thereof include phenyl, 2-methylphenyl, 3-methylphenyl, 4-methylphenyl, 2-methoxyphenyl, 3-trifluoromethylphenyl, pentafluorophenyl, 1-naphtyl, 2-naphtyl and the like.

A heterocyclic group represented by $R^{B2}$ include the group of a monocyclic or condensed cyclic ring having preferably 1 to 20 carbon atoms, more preferably 1 to 12 carbon atoms, further more preferably 2 to 10 carbon numbers, and preferably an aromatic heterocyclic group containing at least one selected from the group consisting of a nitrogen atom, an oxygen atom, a sulfur atom and a selenium atom. Specific examples thereof include pyrrolidine, piperidine, piperadine, morpholine, thiophene, selenophen, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthylzine, quinoxaline, quinazoline, cinnoline, pteridine, acridine, phenanthroline, phenazine, tetrazole, benzimidazole, benzoxazole, benzthiazole, benztriazole, tetraazainndene, carbazol, azepine and the like. Among those, furan, thiophen, pyridine, pyrazine, pyrimidine, pyridazine, triazine, quinoline, phthalazine, naphthylizine; quinoxaline and quinazoline are preferable, furan, thiophen, pyridine and quinoline are more preferable, and quinoline is further more preferable.

The aliphatic hydrocarbon group, the aryl group and the heterocyclic group represented by $R^{B2}$ may have substituent and include the similar ones to the aforementioned in the $L^B$.

$R^{B2}$ includes preferably an alkyl group, an aryl group and an aromatic heterocyclic group, more preferably an aryl group and an heterocyclic group, and further more preferably an aryl group.

$X^{B2}$ includes preferably —O— and =N—$R^{B2}$, more preferably =N—$R^{B2}$, further more preferably =N—$Ar^{B2}$: wherein $Ar^{B2}$ includes an aryl group having 6 to 30 carbon atoms, more preferably 6 to 20 carbon atoms, and further more preferably 6 to 12 carbon atoms, and an aromatic heterocyclic group having preferably 1 to 20 carbon numbers, more preferably 1 to 12 carbon atoms and further more preferably 2 to 10 carbon atoms, and preferably an aryl group.

$Z^{B2}$ represents an atomic family required to form an aromatic ring. The aromatic rings formed by $Z^{B2}$ may be any one of an aromatic hydrocarbon ring and an aromatic heterocycle. Specific examples include, for example, a benzene ring, a pyridine ring, a pyradine ring, a pyrimidine ring, a pyridazine ring, a triazine ring, a pyrrole ring, a furan ring, a thiophene ring, a selenophene ring, a tellurophene ring, an imidazole ring, a thiazole ring, a selenazole ring, a tellurazole ring, a thiadiazole ring, an oxadiazole ring, and a pyrazole ring, preferably a benzene ring, a pyridine ring, a pyradine ring, a pyrimidine ring, and a pyridazine ring, more preferably a benzene ring, a pyridine ring and a pyradine ring, further more preferably a benzene ring and a pyridine ring, in particular preferably a pyridine ring. The aromatic rings formed by $Z^{B2}$ may be linked further to another ring to form a condensed ring and may have substituent. Examples of the substituent include preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxycarbonyl group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano atom and a heterocyclic group, more preferably an alkyl group, an aryl group, an alkoxy group, an aryloxy group, a halogen atom, a cyano group and a heterocylic group, further more preferably an alkyl group, an aryl group, an alkoxy group, an aryloxy group and an aromatic heterocyclic group, in particular preferably an alkyl group, an aryl group, an alkoxy group and an aromatic heterocyclic group.

$n^{B2}$ is an integer of from 1 to 4, and preferably from 2 to 3.

The compounds represented by the following general formula (B-II) are preferable among the compounds represented the above general formula (B-I):

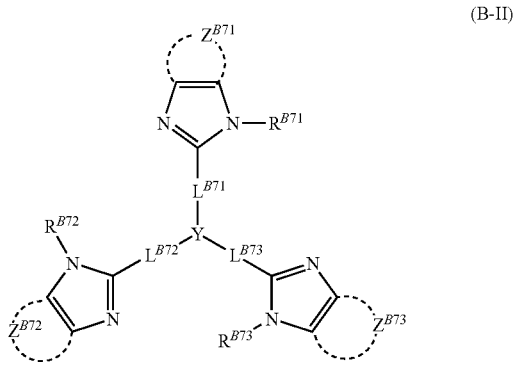

(B-II)

wherein $R^{B71}$, $R^{B72}$ and $R^{B73}$ each in the general formula (B-II) is the same with $R^{B72}$ in the general formula (B-I), and also the preferable range thereof is similar thereto. $Z^{B71}$, $Z^{B72}$ and $Z^{B73}$ each is similar to $Z^{B2}$ in the general formula (B-I), and also the preferable range thereof is similar thereto. $L^{B71}$, $L^{B72}$ and $L^{B73}$ each represents a connecting group, and includes bivalent derivatives derived from the examples of $L^B$ in the general formula (B-I). Preferable one is a connecting bond consisting of a single bond, a bivalent aromatic hydrocarbon ring group, a bivalent aromatic heterocyclic group and a combination thereof, and more preferable one is a single bond. $L^{B71}$, $L^{B72}$ and $L^{B73}$ may have substituents, and the substituents include the similar ones to those of $L^B$ in the general formula (B-I). Y represents a nitrogen atom, a 1,3,5-benzenetriyl group or a 2,4,6-triazinetriyl group. The 1,3,5-benzentriyl group may have substituent at 2,4,6-positions thereof, and the substituent includes, for example, an alkyl group, an aromatic hydrocarbon ring group, a halogen atom and the like.

Specific examples of the nitrogen-containing 5-members derivatives represented by the general formulae (B-I) or (B-II) will be shown as follows, which do not limit the scope of it.

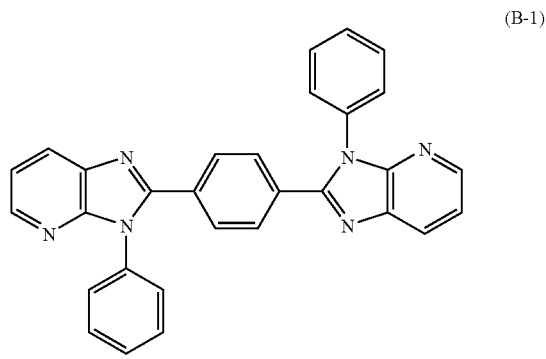

(B-1)

-continued
(B-2)
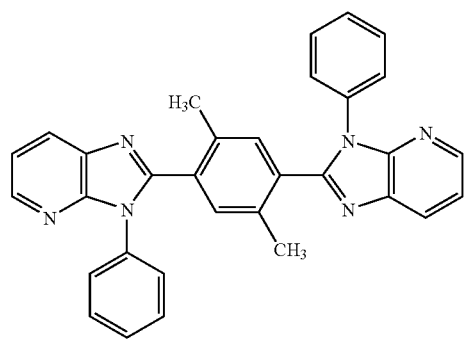
(B-3)
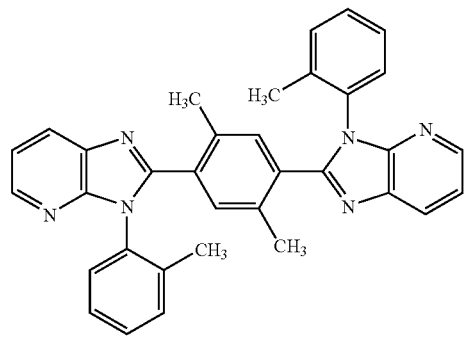
(B-4)
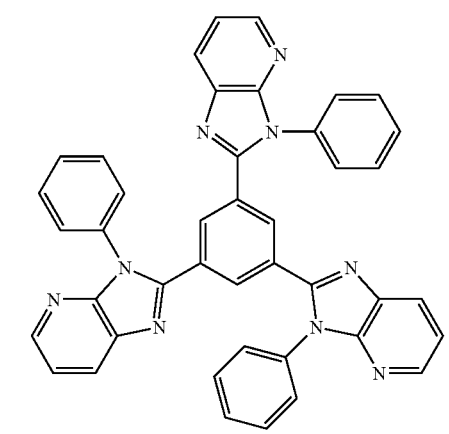
(B-5)
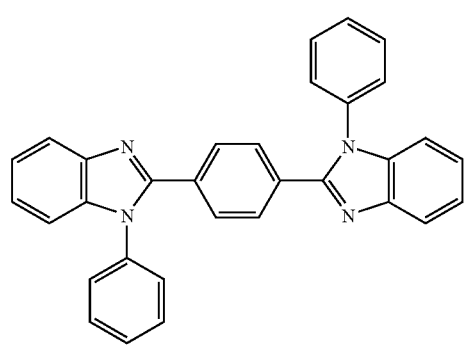
-continued
(B-6)
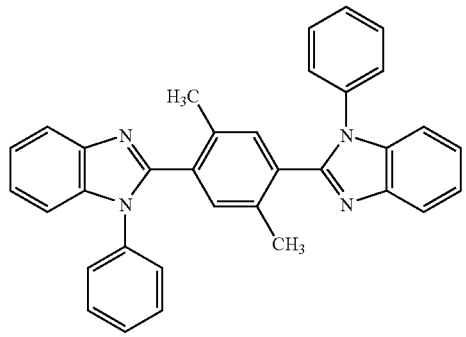
(B-7)
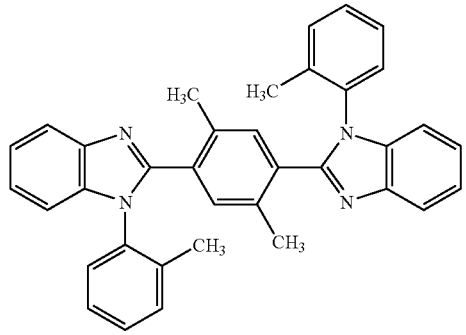
(B-8)
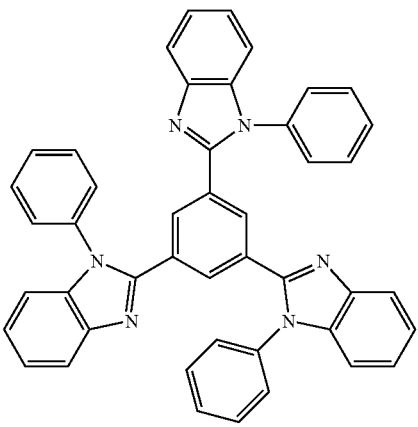
(B-9)
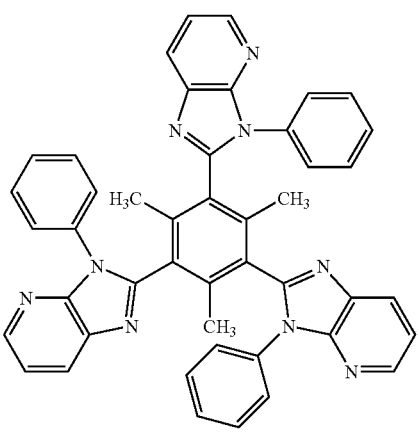

-continued

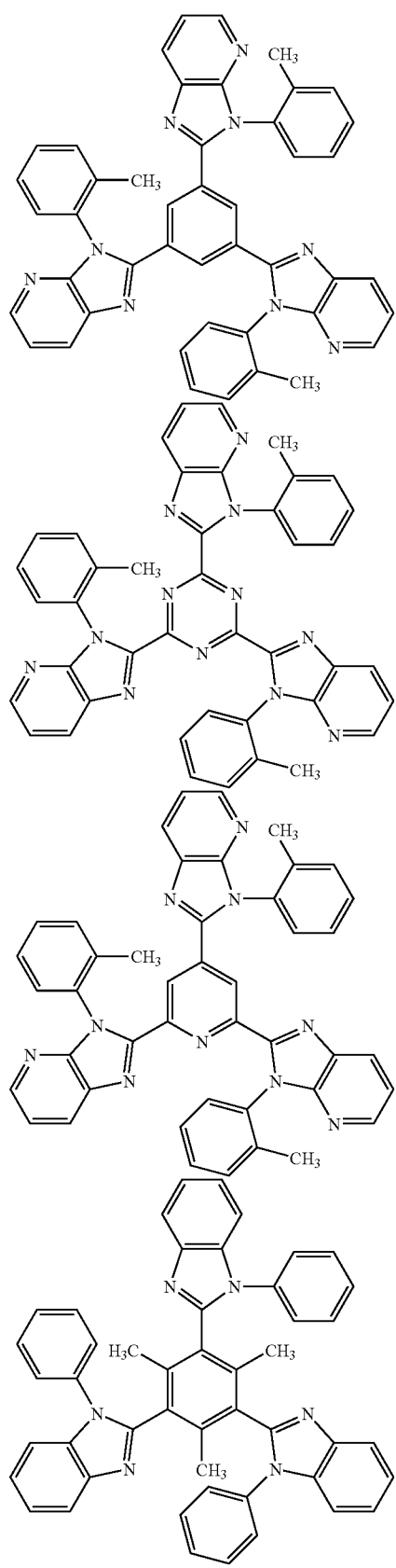

(B-10)
(B-11)
(B-12)
(B-13)

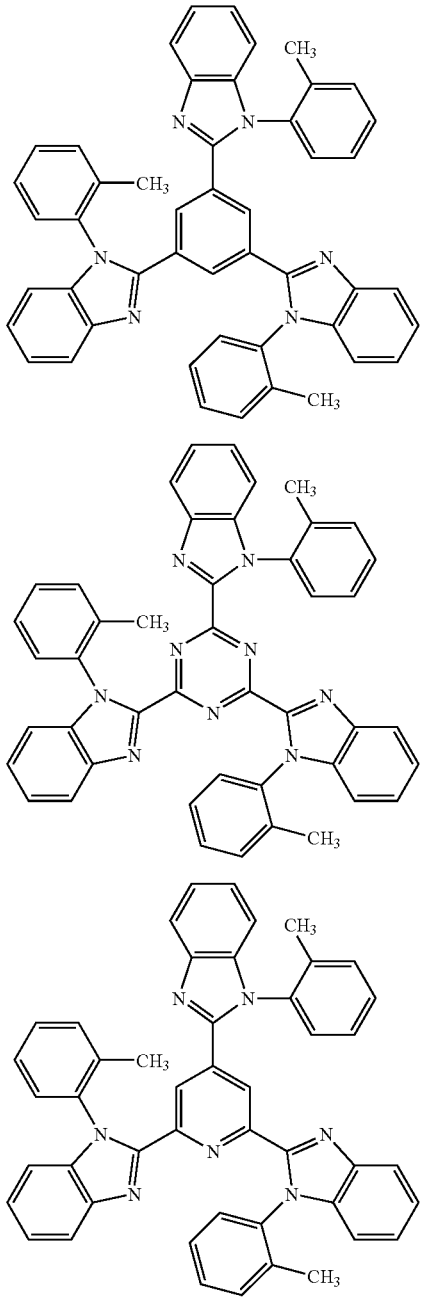

(B-14)
(B-15)
(B-16)

$$(Cz-)_n A \quad \text{(C-I)}$$

$$Cz(-A)_m \quad \text{(C-II)}$$

wherein Cz represents a substituted or unsubstituted carbazolyl group, an arylcarbazolyl group or a carbazolylalkylene group, and A represents a group formed from a moiety represented by the following general formula (A), n and m each represents an integer from 1 to 3.

$$(M)_p\text{-}(L)_q\text{-}(M')_r \quad \text{(A)}$$

wherein, M and M' each independently represents a nitrogen-containing heteroaromatic ring having 2 to 40 carbon atoms of forming a ring, and the ring may have a substituent.

In addition, M and M' may be the same with or different from each other. L represents a single bond, an arylene group having 6 to 30 carbon atoms, a cycloalkylene having 5 to 30 carbon atoms or a heteroaromatic ring having 2 to 30 carbon atoms, and may has a substituent bonding to the ring. p represents an integer from 0 to 2, q represents an integer from 1 to 2 and r represents an integer from 0 to 2, with the proviso that p+r is 1 or larger.

The bonding mode of the general formulae (C-I) and (C-II) is shown as follows depending on the number of index n and m;

TABLE 1

| n = m = 1 | n = 2 | n = 3 | m = 2 | m = 3 |
|---|---|---|---|---|
| Cz—A | Cz—A—Cz | Cz—A—Cz<br>       \|<br>       Cz | A—Cz—A | A—Cz—A<br>       \|<br>       A |

In addition, the bonding mode of the group represented by the general formulae (A) is shown as (1) to (16) in the Tables depending on the number of index p, q and r;

TABLE 2

| No | p | q | r | Bonding mode |
|---|---|---|---|---|
| (1) | 0 | 1 | 1 | L—M' |
| (2) | 0 | 1 | 2 | L—M'—M', M'—L—M' |
| (3) | 0 | 2 | 1 | L—L—M', L—M'—L |
| (4) | 0 | 2 | 2 | L—L—M'—M', M'—L—L—M',<br>L—M'—M'—L, M'—L—M', L—M'—L<br>                              \|                \|             \|<br>                              L                L             M' |
| (5) | 1 | 1 | 0 | the same as (1) (replacing M' with M) |
| (6) | 1 | 1 | 1 | M—L—M' |
| (7) | 1 | 1 | 2 | M—L—M'—M', M—L—M'<br>                                         \|<br>                                         M' |
| (8) | 1 | 2 | 0 | the same as (3) (replacing M' with M) |
| (9) | 1 | 2 | 1 | M—L—L—M', L—M—L—M', M—L—M'—L |

TABLE 3

| (10) | 1 | 2 | 2 | M—L—L—M'—M', M'—L—M—L—M',<br>M'—M'—L—M—L,<br><br>M—L—L,  M—L—L—M',<br>     \|   \|           \|<br>    M' M'         M'<br><br>L—L—M'—M', L—M—L—M',<br>\|                         \|<br>M                        M'<br><br>       M'<br>       \|<br>M—L—L<br>       \|<br>       M' |
| (11) | 2 | 1 | 0 | the same as (2) (replacing M' with M) |
| (12) | 2 | 1 | 1 | the same as (7) (replacing M' with M) |

TABLE 3-continued

| (13) | 2 | 1 | 2 | M—M—L—M'—M',<br><br>           M'<br>           \|<br>M—L—M,  M—L—M'—M'<br>           \|<br>           M' |
| (14) | 2 | 2 | 0 | the same as (4) (replacing M' with M) |
| (15) | 2 | 2 | 1 | the same as (10) (replacing M' with M) |
| (16) | 2 | 2 | 2 | M—M—L—L—M'—M',<br><br>M—M—L—M'—M',<br>           \|<br>           L<br><br>M—L—L—M'—M',<br>     \|<br>     M<br><br>     M<br>     \|<br>M—L—L,  M—M—L—L—M',<br>   / \                \|<br>M'  M'            M'<br><br>     M<br>     \|<br>L—L—M'—M',  M—L—L—M<br>     \|                           \|  \|<br>     M                        M' M' |

In the above general formulae (C-I) and (C-II), Cz may be linked to any part of M, L and M' representing A when Cz bonds to A. For example, in the case of Cz-A of m=n=1 and of p=q=r=1 ((6) in Table), A is M-L-M', and tree bonding modes of Cz-M-L-M', M-L(-Cz)-M' and M-L-M'-Cz can be shown. Similarly, for example, in Cz-A-Cz which is n=2 of the general formula (C-I), and in the case of p=q=1 and r=2 ((7) in Table), A is M-L-M'-M or M-L(-M')-M' and represented by the following bonding modes:

Cz—M—L—M'—M',     Cz—M—L—M'—M',
       \|                                    \|
       Cz                                   Cz
Cz—M—L—M'—M'      Cz—M—L—M'—M'—Cz,
           \|
           Cz
       Cz
       \|
M—L—M'—M',               M—L—M'—M'
   \|                                \|   \|
   Cz                              Cz  Cz
M—L—M'—M'—Cz,          M—L—M'—M',
   \|                                \|
   Cz                              Cz
M—L—M'—M'—Cz              M—L—M'—M'—Cz,
   \|                                \|
   Cz                              Cz
Cz—M—L—M',                Cz—M—L—M',
           \|   \|                            \|
           Cz M'                          M'
                Cz   Cz                 Cz
                  \ /                     \|
Cz—M—L—M'    L—L—M',    M—L—M'—Cz
   \|                \|                   \|
   M'              M'                 M'
   \|
   Cz

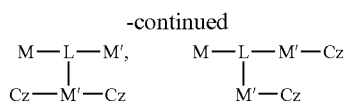
Specific examples represented by the above general formulae (C-I) and (C-II) include the following structures, but not limited thereto;
(C-1)
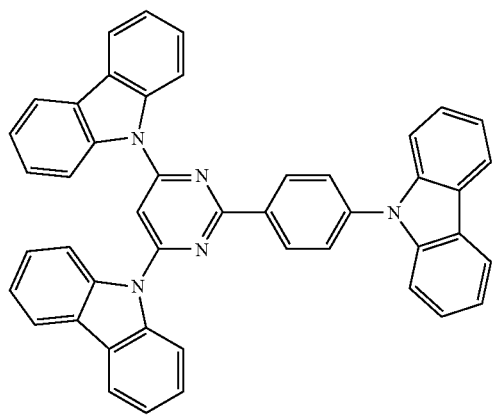
(C-2)
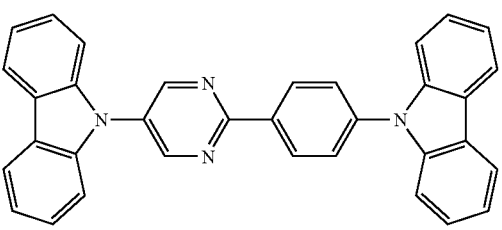
(C-3)
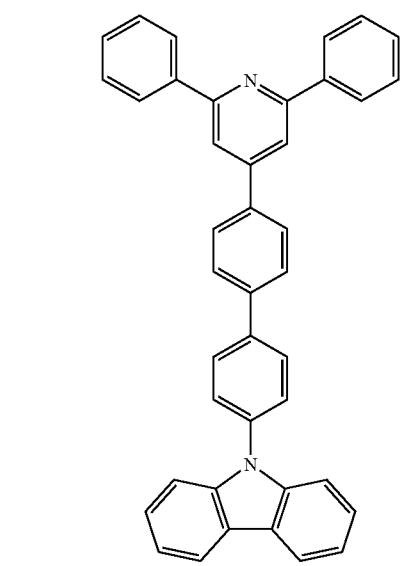
(C-4)
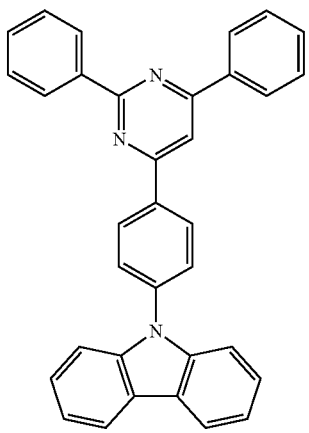
(C-5)
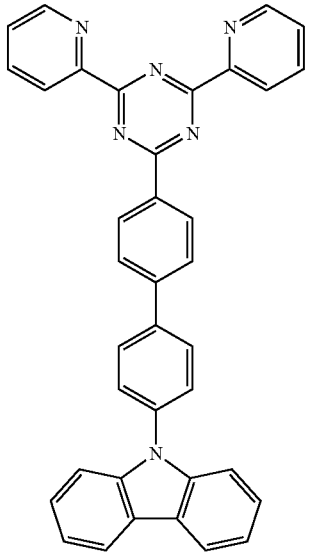
(C-6)
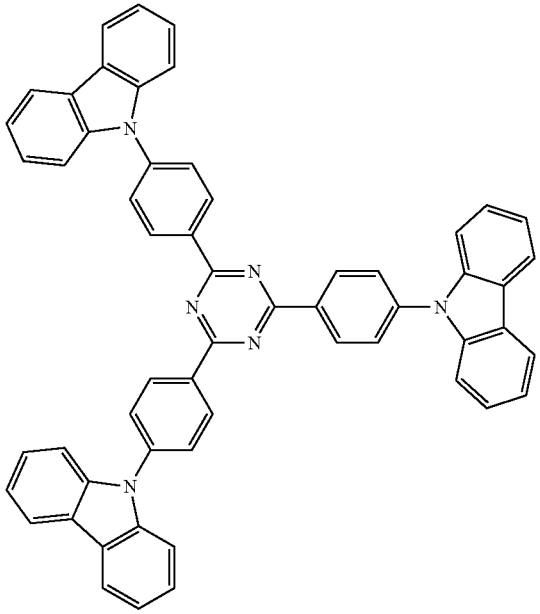

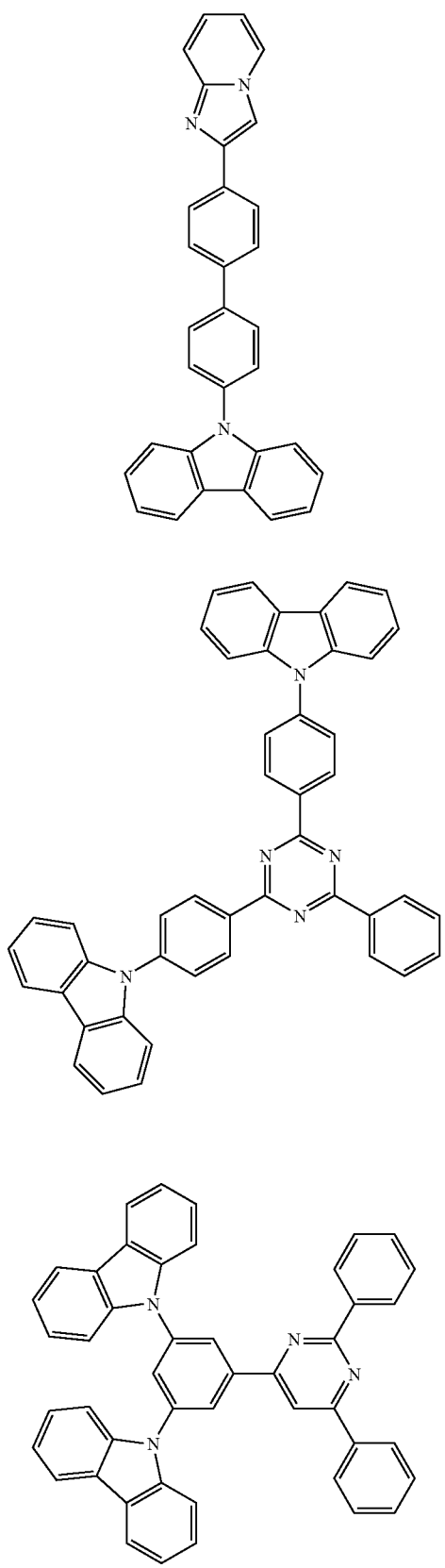
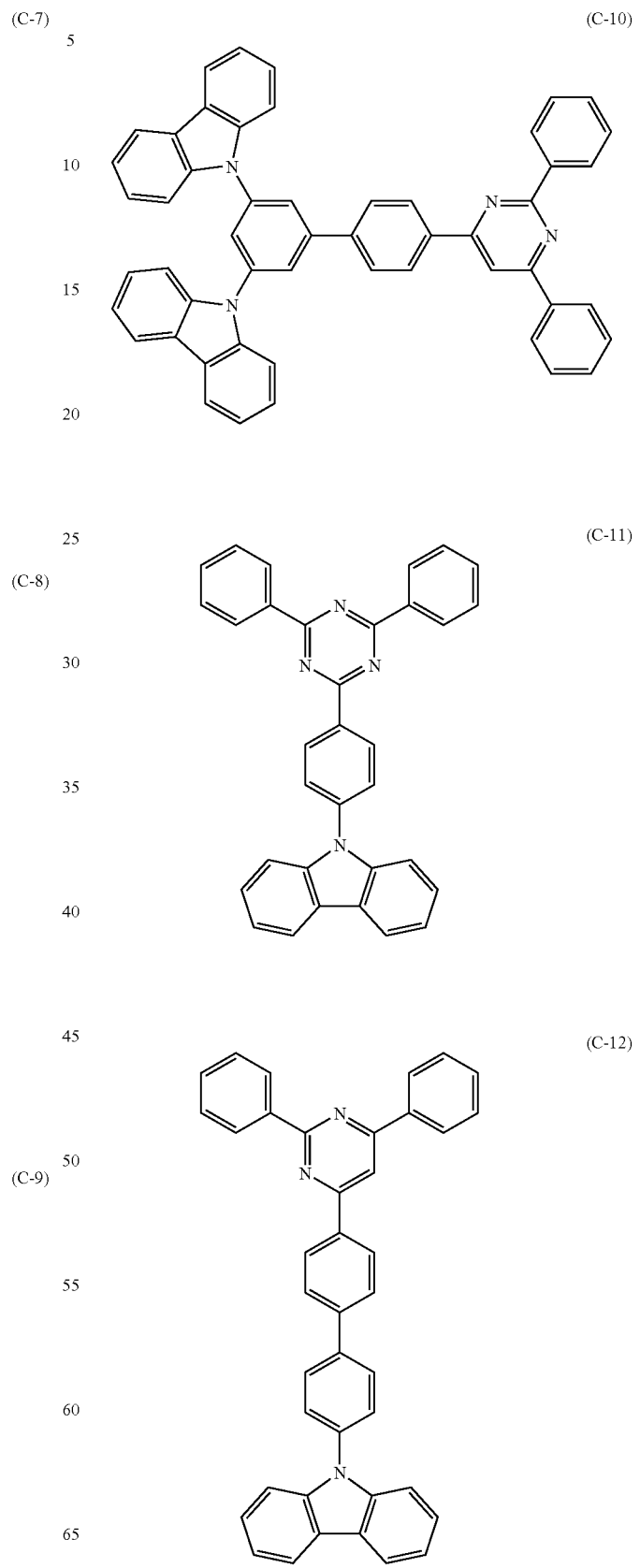

-continued

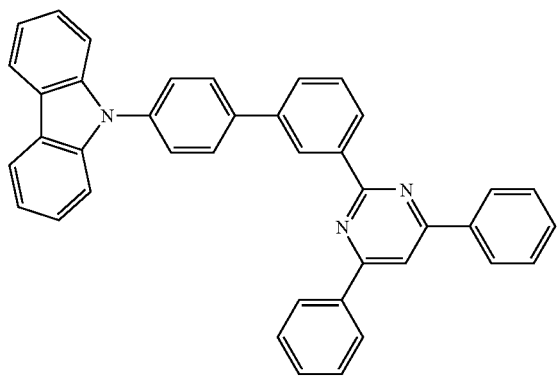
(C-13)

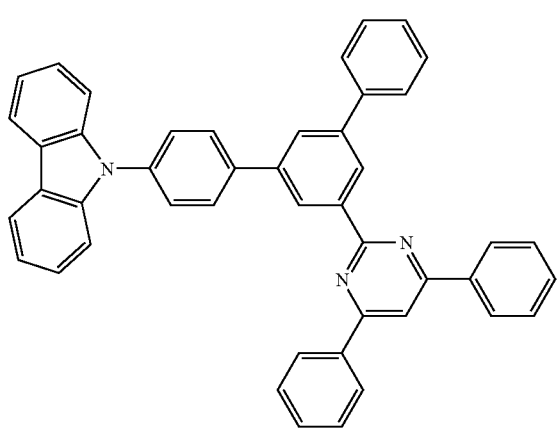
(C-14)

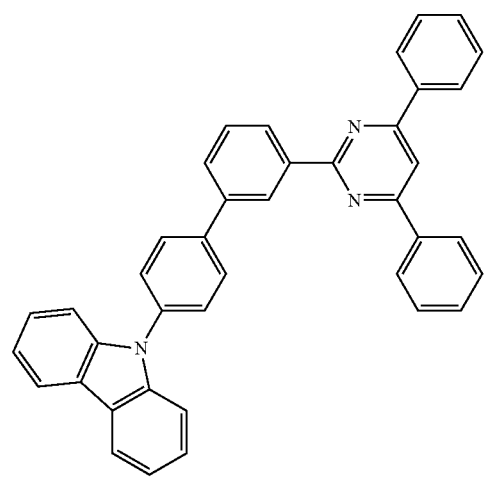
(C-15)

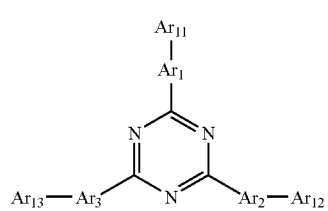
(C-III)

wherein, $Ar_{11}$ to $Ar_{13}$ each represents the similar groups to those of $R^{B2}$ in the general formula (B-I), and specific examples thereof are similar thereto. $Ar_1$ to $Ar_3$ represent bivalent derivatives derived from the groups similar to those of $R^{B2}$ in the general formula (B-I) and specific examples thereof are similar thereto.

Example of the general formula (C-III) is shown as follows, but not limited thereto;

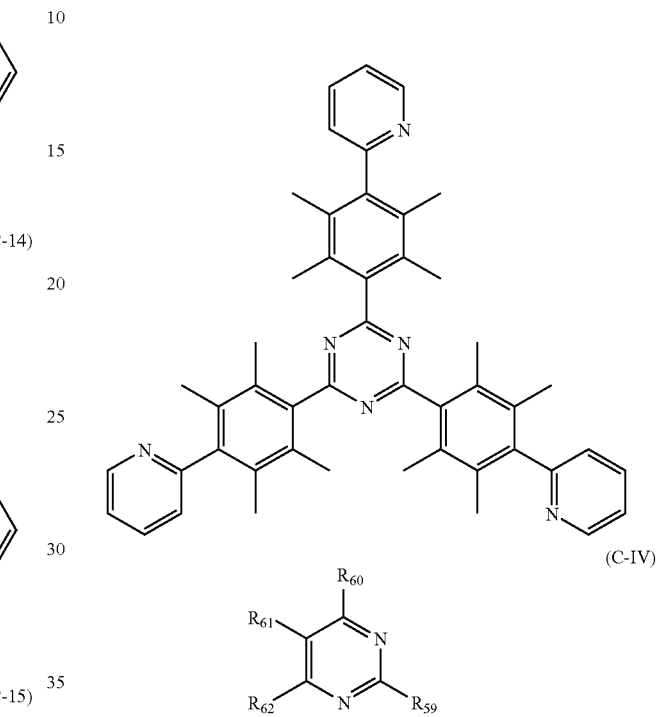
(C-IV)

wherein, $R_{56}$ to $R_{62}$ each represents the similar groups to those of $R^{B2}$ in the general formula (B-I), and specific examples thereof are similar thereto.

Example of the general formula (C-IV) is shown as follows, but not limited thereto;

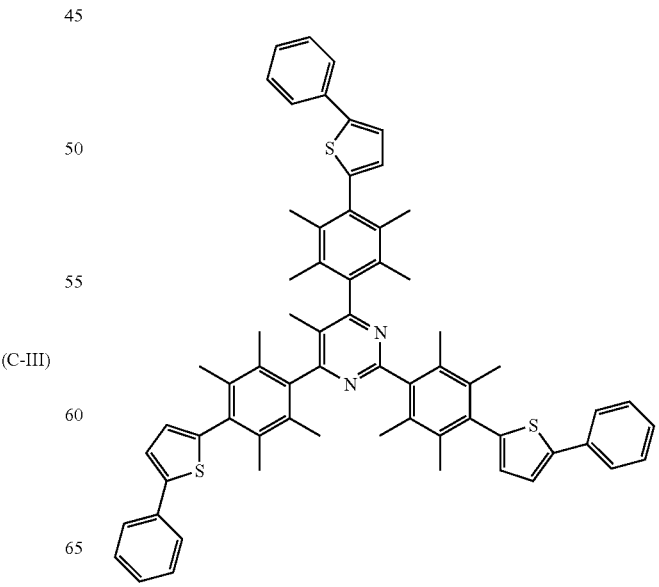

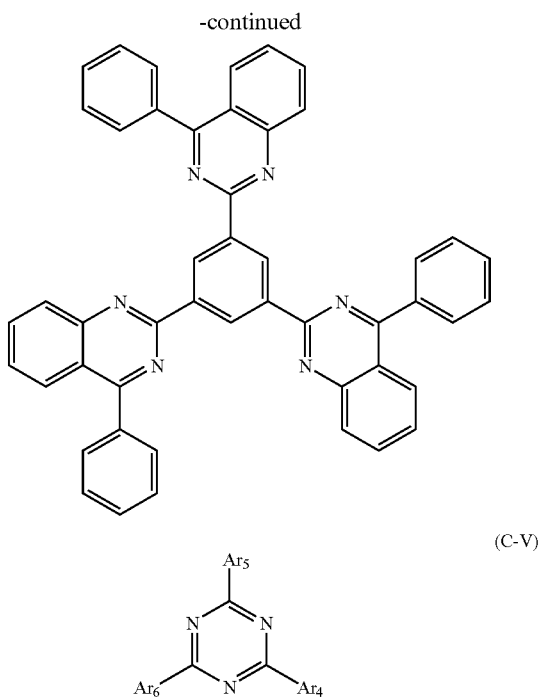

(C-V)

wherein, $Ar_5$ to $Ar_7$ each represents the similar groups to those of $R^{B2}$ in the general formula (B-I), and specific examples thereof are similar thereto.

Example of the general formula (C-V) is shown as follows, but not limited thereto;

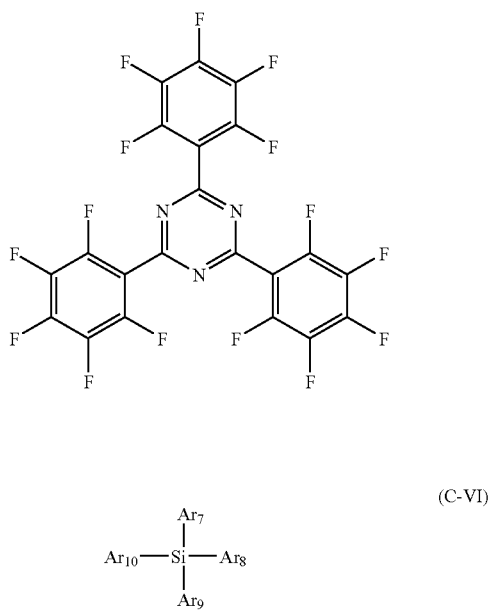

(C-VI)

wherein, $Ar_7$ to $Ar_{10}$ each represents the similar groups to those of $R^{B2}$ in the general formula (B-I), and specific examples thereof are similar thereto.

Example of the general formula (C-VI) is shown as follows, but not limited thereto;

In addition, it is preferable to employ an inorganic compound of insulator or semiconductor as a material constituting an electron injecting or transporting layer in the organic EL device of the present invention. When the electron injecting or transporting layer comprises the above insulator or semiconductor, it is possible to prevent the leakage of the electric current effectively and the electron injecting capability can be improved. It is preferable that at least one metal compound selected from the group consisting of alkali metal chalcogenides, alkaline earth metal chalcogenides, alkali metal halides and alkaline earth metal halides is used as the insulator. It is preferable that the electron injecting or transporting layer comprises the above alkali metal chalcogenide and the like since the electron injecting capability can be improved.

Preferable examples of the alkali metal chalcogenide include $Li_2O$, $Na_2S$, $Na_2Se$ and the like. Preferable examples of the alkaline earth metal chalcogenide include CaO, BaO, SrO, BeO, BaS and CaSe. Preferable examples of the alkali metal halide include LiF, NaF, KF, LiCl, KCl, NaCl and the like. Preferable examples of the alkaline earth metal halide include fluorides such as $CaF_2$, $BaF_2$, $SrF_2$, $MgF_2$ and $BeF_2$ and halides other than the fluorides.

Examples of the semiconductor constituting the electron injecting or transporting layer include oxides, nitrides and oxide nitrides containing at least one element selected from Ba, Ca, Sr, Yb, Al, Ga, In, Li, Na, Cd, Mg, Si, Ta, Sb and Zn, which are used singly or in combination of two or more. It is preferable that the inorganic compound constituting the electron transporting layer is in the form of a microcrystalline or amorphous insulating thin film. When the electron transporting layer comprises the above insulating thin film, a more uniform thin film can be formed and pixel defect such as dark spots can be decreased. Examples of the inorganic compound include the alkali metal chalcogenides, the alkaline earth metal chalcogenides, the alkali metal halides and the alkaline earth metal halides which are described above.

In addition, at least any one of the electron injecting layer and electron transporting layer of the organic EL device of the present invention may contain a reductive dopant with the work function of 2.9 eV or less. In the present invention, the reductive dopant means compounds which increase the electron injecting efficiency.

Further, it is preferable in the present invention that a reductive dopant is added into an interface area between the cathode and the organic thin film layer. The dopant reduces at least one part of the organic layer contained in the interface area to form anion. Preferable examples of the reductive dopant include at least one compound selected from the group consisting of alkali metals, alkali metal oxides, alkaline earth metals, rare earth metals, alkali metal oxides, alkali metal halides, alkaline earth metal oxides, alkaline earth metal halides, rare earth metal oxides, rare earth metal halides, alkali metal complexes, alkaline earth metal complexes and rare earth metal complexes. Specific examples of the preferable reductive dopant include at least an alkali metal selected from the group consisting of Na (the work function: 2.36 eV), K (the work function: 2.28 eV), Rb (the work function: 2.16 eV) and Cs (the work function: 1.95 eV), or at least an alkaline earth metal selected from the group consisting of Ca (the work function: 2.9 eV), Sr (the work function: 2.0 to 2.5 eV) and Ba (the work function: 2.52 eV), and whose work function of 2.9 eV or less is particularly preferable. Among those dopants, an alkali metal selected from the group consisting of K, Rb and Cs is more preferable, and Rb and Cs are further more preferable. Cs is most preferable. The alkali metals have particularly high reducing capability so that addition of them in small quantity into an electron injecting zone results in improvement of luminance of emitted light as well as a longer lifetime.

The alkaline earth metal oxides include preferably, for example, BaO, SrO, CaO, and the mixtures thereof having the structures of $Ba_xSr_{1-x}O$ (0<x<1) and $Ba_xCa_{1-x}O$ (0<x<1). The alkali oxides or alkali fluorides include LiF, $Li_2O$, NaF and the like. It is not limited for the alkali metal complexes, alkaline earth metal complexes and rare earth metal complexes when these complexes contain at least a metal ion of alkali metal ion, alkaline earth metal ion and rare earth metal ion. In addition, examples of the ligand include, for example, quinolinol, benzoquinolinol, acridinol, phenanthridinol, hydroxyphenyloxazole, hydroxyphenylthiazol, hydroxydiaryloxazole, hydroxydiarylthiazol, hydroxyphenylpyridine, hydroxyphenylbenzimidazole, hydroxybenztriazole, hydroxyfluborane, bipyridyl, phenanthroline, phthalocyanine, porphyrin, cyclopentadiene, β-diketones, azomethine and derivatives thereof, but not limited thereto.

It is preferable to form the reductive dopants in a layer shape or in an island shape. The preferable thickness of the layer shape is from 0.05 to 8 nm.

As a forming process of the electron injecting or transporting layer containing a reductive dopant thereof, it is preferable that organic materials of a light emitting material or an electron injecting material forming an interface area are deposited while depositing a reductive dopant by a resistive heating vapor deposition process and the reductive dopant is dispersed into the organic materials. The dispersion concentration is in the range from 100:1 to 1:100, preferably 5:1 to 1:5 by mole ratio. When forming the reductive dopant in a layer shape, a light emitting material or an electron injecting material is formed in a layer shape, followed by depositing the reductive dopant singly by a resistive heating vapor deposition process so as to form the layer having preferably a thickness of 0.1 to 15 nm. When forming the reductive dopant in a island shape, a light emitting material or an electron injecting material of an organic layer at the interface is formed, followed by depositing the reductive dopant singly by a resistive heating vapor deposition process so as to form the layer having preferably a thickness of 0.05 to 1 nm.

When an electric field is applied to the organic EL device of the present invention, the light emitting layer has the function of injecting holes from the anode or the hole injecting layer, the function of injecting electrons from the cathode or the electron injecting layer, the function of transporting injected charges (electrons and holes) by the force of the electric field, and the function of providing the field for recombination of electrons and holes in order to lead the recombination to the emission of light. It is preferable for the light emitting layer of the organic EL device to contain at least a metal complex compound of the present invention and also a host material, of which a guest material is the metal complex compound. The above host material includes, for example, a compound having a carbazole framework, a diarylamine framework, a pyridine framework, a pyrazine framework, a triazine framework, an arylsilane framework and the like. It is preferable for T1, which is a energy level at the minimum triplet excited state, of the host materials is larger than T1 of the guest materials. The host materials may be a low molecular weight compound or a high molecular weight compound. In addition, it is possible to form a light emitting layer having the light emitting material doped in the host material by a co-deposition or the like with the host material and a light emitting material of the metal complex compounds and the like.

In the organic EL device of the present invention, there is no imitation for a forming process of the layers described above, but it is possible to employ various processes such as a vacuum vapor deposition process, a LB process, a resistive heating vapor deposition process, an electron beam process, a sputtering process, a molecular lamination process, a conventional coating process such as the spin coating process, the casting process, the dipping coating process and the like, an inkjet process and a printing process. The coating process as an application process is preferable for the present invention.

In addition, the organic thin film layer comprising the metal complex compound of the present invention can be formed in accordance with the vacuum vapor deposition process, the molecular beam epitaxy process (the MBE process) or, using a solution prepared by dissolving the compound into a solvent, in accordance with a conventional coating process such as the dipping process, the spin coating process, the casting process, the bar coating process and the roller coating process.

In the above coating processes, it is possible to prepare an embrocation by dissolving the metal complex compound into a solvent, followed by applying it on the desired layer or the electrode and dried. It is possible to have a resin contained in the embrocation, and the resin may be dissolved or dispersed in the solvent. A non-conjugated type polymer such a polyvinylcarbazole and a conjugated type polymer such as polyolefine may be used. Specific examples thereof include, for example, polyvinylchloride, polycarbonate, polystyrene, polymethylmethacrylate, polybutylmethacrylate, polyester, polysulfone, polyphenyleneoxide, polybutadiene, poly(N-vinylcarbazole), hydrocarbon resin, ketone resine, phenoxy resin, polyamide, ethyl cellulose, vinyl acetate, ABS resin, polyurethane, melamine resin, unsaturated polyester resin, alkyd resin, epoxy resin, and silicone resin.

Additionally, the film thickness of each organic layer in the organic EL device of the present invention is not particularly limited, but, there is a general tendency of causing defects such as a pin-hole when it is too thin, adversely there is a tendency of lowing efficiency due to high voltage charged when it is too thick; therefore, a thickness in the range of from several nanometers to 1 μm is preferable.

EXAMPLE

This invention will be described in further detail with reference to the examples.

Synthesis Example 1

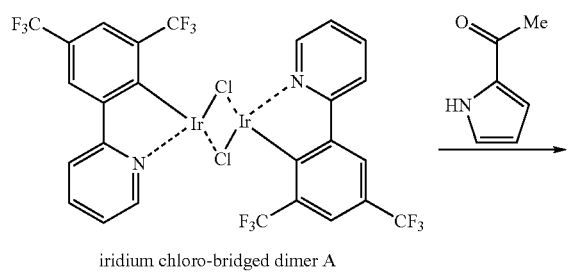

iridium chloro-bridged dimer A

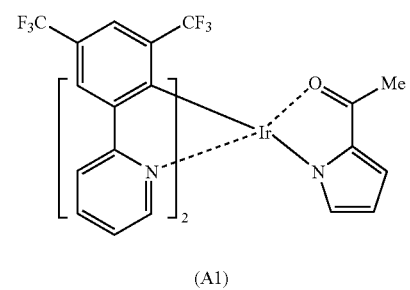

(A1)

Synthesis of Compound (A1)

2.00 g of iridium chloro-bridged dimer A, 0.34 g of 2-acetylpyrrole, 1.7 g of sodium carbonate and 50 ml of 2-ethoxyethanol were placed in a three neck flask of 200 ml, followed by the argon gas displacement, and the resultant was refluxed under heating for 10 hours while stirring. The resultant was cooled to a room temperature, followed by filtration. The obtained-solid substance was added dichloromethane and water, followed by dichloromethane extraction. The organic solvent layer was dried with the use of sodium sulfate anhydride, followed by evaporation. The obtained was purified with 100 g of silica gel column chromatography and as a result, slightly yellow colored solid of 2.0 g was obtained. Further, it was purified by sublimation under the vacuum of $50 \times 10^{-6}$ Torr at 250 degC, and 1.93 g of the compound (A1) was obtained. The structure was identified by FD-MS measurement (Field Desorption Mass Spectrometry). The result of the measurement is shown as follows:

FD-MS: calcd. for $IrC_{32}H_{19}F_{12}N_{30}$=881, found, m/z=881 (100)

Synthesis Example 2

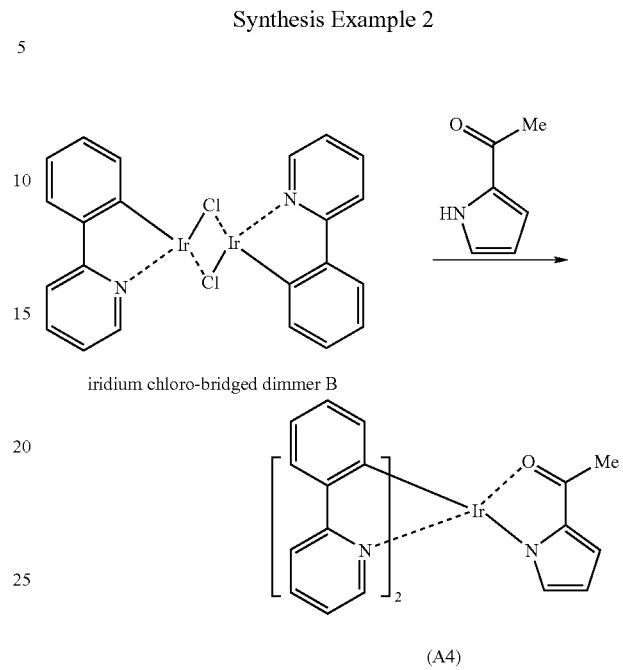

iridium chloro-bridged dimmer B (A4)

Synthesis of Compound (4)

2.40 g of iridium chloro-bridged dimer B, 0.36 g of 2-acetylpyrrole, 1.60 g of sodium carbonate and 50 ml of 2-ethoxyethanol were placed in a three neck flask of 200 ml, followed by the argon gas displacement, and the resultant was refluxed under heating for 9 hours while stirring. The resultant was cooled to a room temperature, followed by filtration. The obtained-solid substance was added dichloromethane and water, followed by dichloromethane extraction. The organic layer was dried with the use of sodium sulfate anhydride, followed by evaporation. The obtained was purified with 100 g of si ca gel column chromatography and as a result, slightly yellow colored solid of 1.75 g was obtained. Further, it was purified by sublimation under the vacuum of $4.0 \times 10^{-6}$ Torr at 280 deg C., and 1.41 g of the compound (A4) was obtained. The structure was identified by FD-MS measurement. The result of THE measurement is shown as follows:

FD-MS: calcd. for $IrC_{28}H_{22}IrN_{30}$=609, found, m/z=609 (100)

Synthesis Example 3

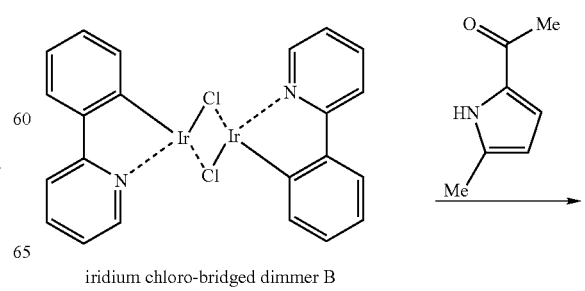

iridium chloro-bridged dimmer B

-continued

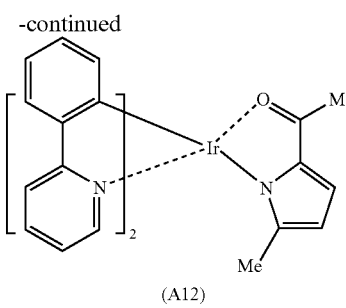

(A12)

Synthesis of Compound (A12)

2.20 g of iridium chloro-bridged dimer B, 0.42 g of 2-acetyl-5-methylpyrrole, 1.60 g of sodium carbonate and 50 ml of 2-ethoxyethanol were placed in a three neck flask of 200 ml, followed by the argon gas displacement, and the resultant was refluxed under heating for 16 hours while stirring. The resultant was cooled to a room temperature, followed by filtration. The obtained-solid substance was added dichloromethane and water, followed by dichloromethane extraction. The organic layer was dried with the use of sodium sulfate anhydride, followed by evaporation. The obtained was purified with 100 g of silica gel column chromatography and as a result, slightly yellow colored solid of 1.60 g was obtained. Further, it was purified by sublimation under the vacuum of $3.6 \times 10^{-6}$ Torr at 260 deg C., and 1.38 g of the compound (A12) was obtained. The structure was identified by FD-MS measurement. The result of the measurement is shown as follows:

FD-MS: calcd. for $C_{29}H_{24}IrN_{30}$=623, found, m/z=623 (100)

Example 1

Fabrication Example 1 of an Organic EL Device

A glass substrate of 25 mm×75 mm×0.7 mm thickness having an ITO transparent electrode was cleaned by application of ultrasonic wave in isopropyl alcohol for 5 minutes, and then exposed to ozone generated by ultraviolet light for 30 minutes. The cleaned glass substrate having the ITO transparent electrode was fixed to a substrate holder of a vacuum deposition apparatus, and on a surface of the substrate, on which the ITO transparent electrode was formed, a film of TPD232 of the following formula was formed so as to cover the transparent electrode. The film thickness was 85 nm. The TPD232 film performs as a hole injecting layer. Subsequently, on the TPD232 film, a layer having layer thickness of 10 nm of 4,4',4'-tris(carbazole-9-yl)-triphenylamine (TCTA) of the following formula was formed. The TCTA film performs as a hole transporting layer. Subsequently, on the TCTA film, a film having a film thickness of 30 nm of the following compound (H) as a host material was formed for a light emitting layer by vapor deposition. As a phosphorescent Ir metal complex dopant, the metal complex compound (A1) was added together. The content of the metal complex compound (A1) in the light emitting layer was 7.5% by weight. The film performs as a light emitting layer. On the film, a BAlq film of the following formula having a film thickness of 25 nm was formed. The BAlq film performs as an electron transporting layer. Subsequently, on the film, an Alq film of the following formula having a film thickness of 5 nm was formed. The Alq film performs as an electron injecting layer. Then, lithium fluoride was deposited thereon to be a thickness of 0.1 nm, followed by deposition of aluminum of a thickness of 150 nm. The Al/LiF performs as the cathode. Thus an organic EL device was fabricated.

The sealed-device was tested by applying electric current, and the luminance of 102 cd/m² and a blue-green colored emission of CIE chromaticity (0.17, 0.36) were observed and the current efficiency was 17.3 cd/A at the voltage of 6.8 V and the current density of 0.59 mA/cm².

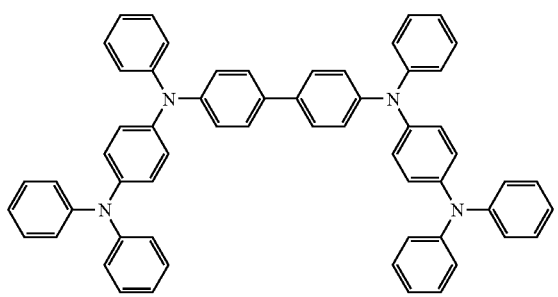
TPD232

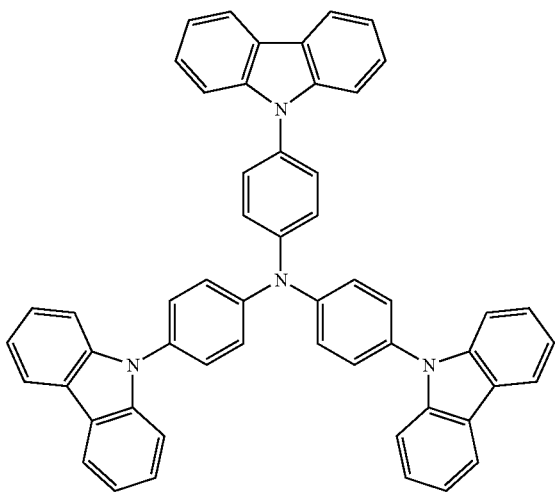
TCTA

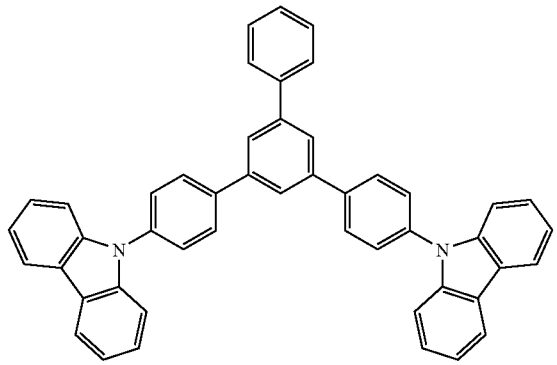
(Compound H)

-continued

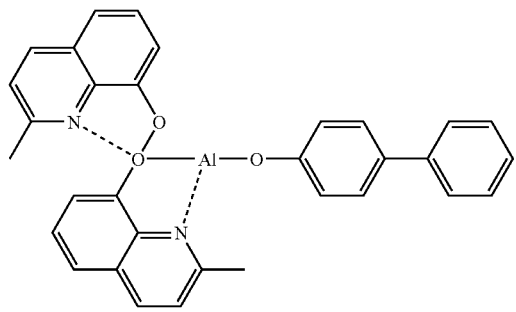
BAlq

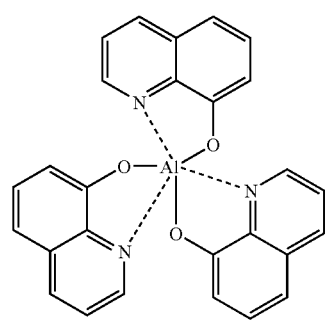
Alq

Comparative Example 1

An organic EL device was fabricated similarly as Example 1 except that Compound D was used in place of (A1) as a dopant.

The sealed-device was tested by applying electric current, and the luminance of 102 cd/m² and a blue-green colored emission of CIE chromaticity (0.18, 0.38) were observed and the current efficiency was 12.8 cd/A at the voltage of 7.5 V and the current density of 0.80 mA/cm².

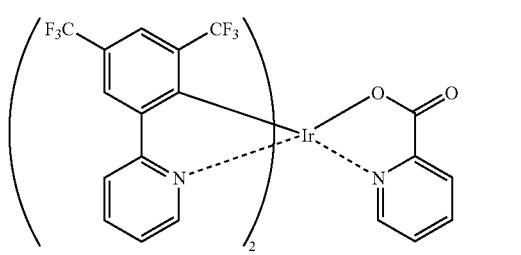
(Compound D)

Example 2

Fabrication Example 2 of an Organic EL Device

A glass substrate of 25 mm×75 mm×0.7 mm thickness having an ITO transparent electrode was cleaned by application of ultrasonic wave in isopropyl alcohol for 5 minutes, and then exposed to ozone generated by ultraviolet light for 30 minutes. The cleaned glass substrate having an ITO transparent electrode was fixed to a substrate holder of a vacuum deposition apparatus, and on a surface of the substrate, on which the ITO transparent electrode was formed, a film of TPD232 of the following formula was formed so as to cover the transparent electrode. The film thickness was 60 nm. The film of TPD232 performs as a hole injecting layer. Subsequently, on the TPD232 film, a layer having layer thickness of 30 nm of TBDB was formed. The TBDB film performs as a hole transporting layer. Subsequently, on the TBDB film, a film having a film thickness of 30 nm of the compound (H) as a host material was formed for a light emitting layer by vapor deposition. As a phosphorescent Ir metal complex dopant, the metal complex compound (A4) was added together. The content of the metal complex compound (A4) in the light emitting layer was 5% by weight. The film performs as a light emitting layer. On the film, the BAlq film having a film thickness of 10 nm was formed. The BAlq film performs as an electron transporting layer. Subsequently, on the fin, the Alq film having a film thickness of 40 nm was formed. The Alq film performs as an electron injecting layer. Then, LiF of alkali halides was deposited thereon to be a thickness of 0.2 nm, followed by deposition of aluminum of a thickness of 150 nm. The Al/LiF performs as the cathode. Thus an organic EL device was fabricated. The sealed-device was tested by applying electric current, and the luminance of 105 cd/m² and a green colored emission of the chromaticity coordinates (0.30, 0.60) were observed and the current efficiency was 35 cd/A at the voltage of 5.4 V and the current density of 0.30 mA/cm².

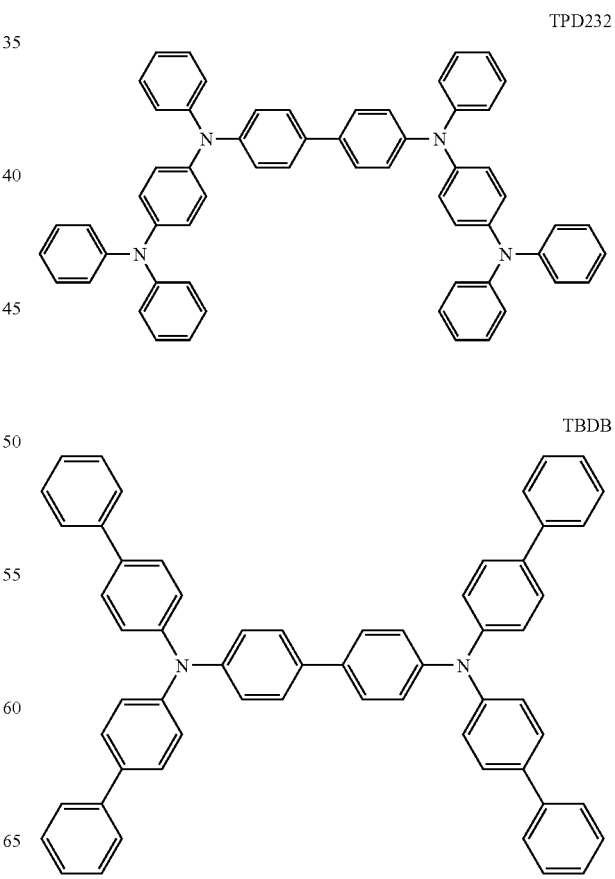

-continued

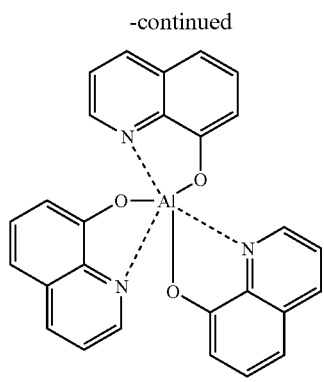

Alq

Example 3

Fabrication Example 3 of an Organic EL Device

An organic EL device was fabricated similarly as Example 2 except that the above metal complex compound (A12) was used in place of the metal complex compound (A4) as the Ir metal complex dopant of the light emitting layer.

The sealed-device was tested by applying electric current, and the luminance of 101 cd/m² and a green colored emission of the chromaticity coordinates (0.30, 0.59) were observed and the current efficiency was 37 cd/A at the voltage of 5.6 V and the current density of 0.27 mA/cm².

Comparative Example 2

An organic EL device was fabricated similarly as Example 2 except that the following compound D2 was used in place of the metal complex compound (A4) as the Ir metal complex dopant of the light emitting layer. The sealed-device was tested by applying electric current, and the luminance of 102 cd/m² and a green colored emission of the chromaticity coordinates (0.30, 0.63) were observed and the current efficiency was 31 cd/A at the voltage of 5.7 V and the current density of 0.33 mA/cm².

(Compound D2)

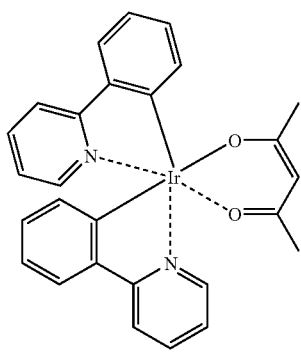

As explained above, the organic EL device having high efficiency and heat resistance can be produced by employing the metal complexes compounds comprising a pyrrole framework as the ligand of dopant.

INDUSTRIAL APPLICABILITY

As aforementioned, the EL device employing the metal complex compounds exhibits high efficiency of light emission and the compounds can be suitable for a material of an organic EL device. Therefore, it is useful for using in the field of a various display devices, a display, a back-light, a light source, a sign, advertising display, interior and the like. It is particularly suitable for a display device for a color display.

The invention claimed is:

1. A metal complex compound represented by formula (1):

$$(L_1)_m M(L_2)_n \qquad (1)$$

wherein M represents a metal atom selected from the group consisting of iridium (Ir), platinum (Pt) and rhodium (Rh), $L_1$ and $L_2$ represent bidentate ligands which are different from each other, the sectional structure $(L_1)_m M$ is represented by formula (4), the sectional structure $M(L_2)_n$ is represented by formula (8), and m and n each represents an integer of 1 or 2, and m+n represents an integer of 2 or 3;

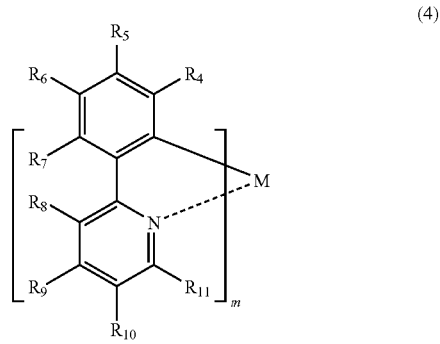

(4)

wherein M and m are as defined in formula (1), $R_4$ to $R_{11}$ each independently represents a hydrogen atom, a substituted or unsubstituted alkyl group having 1 to 30 carbon atoms, a substituted or unsubstituted halogenated alkyl group having 1 to 30 carbon atoms, a substituted or unsubstituted alkoxy group having 1 to 30 carbon atoms, a substituted or unsubstituted heterocyclic group having 3 to 20 ring atoms, a substituted or unsubstituted aryl group having 6 to 40 ring carbon atoms, a substituted or unsubstituted aryloxy group having 6 to 40 ring carbon atoms, a substituted or unsubstituted aralkyl group having 7 to 40 carbon atoms, a substituted or unsubstituted alkenyl group having 2 to 30 carbon atoms, a substituted or unsubstituted arylamino group having 6 to 80 ring carbon atoms, a substituted or unsubstituted alkylamino group having 1 to 60 carbon atoms, a substituted or unsubstituted aralkylamino group having 7 to 80 carbon atoms, a substituted or unsubstituted alkylsilyl group having 1 to 30 carbon atoms, a substituted or unsubstituted arylsilyl group having 6 to 40 carbon atoms, a halogen atom, a cyano group, a nitro group, —S(R)O₂, or —S(R)O; wherein R represents a substituent, and neighboring groups among $R_4$ to $R_{11}$ may be linked to each other to form a saturated or unsaturated ring structure;

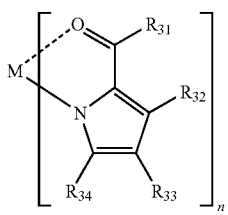

wherein M and n are as defined in formula (1), $R_{31}$ to $R_{34}$ each independently represents a hydrogen atom, a substituted or unsubstituted alkyl group having 1 to 30 carbon atoms, a substituted or unsubstituted halogenated alkyl group having 1 to 30 carbon atoms, a substituted or unsubstituted alkoxy group having 1 to 30 carbon atoms, a substituted or unsubstituted heterocyclic group having 3 to 20 ring atoms, a substituted or unsubstituted aryl group having 6 to 40 ring carbon atoms, a substituted or unsubstituted aryloxy group having 6 to 40 ring carbon atoms, a substituted or unsubstituted aralkyl group having 7 to 40 carbon atoms, a substituted or unsubstituted alkenyl group having 2 to 30 carbon atoms, a substituted or unsubstituted arylamino group having 6 to 80 ring carbon atoms, a substituted or unsubstituted alkylamino group having 1 to 60 carbon atoms, a substituted or unsubstituted aralkylamino group having 7 to 80 carbon atoms, a substituted or unsubstituted alkylsilyl group having 1 to 30 carbon atoms, a substituted or unsubstituted arylsilyl group having 6 to 40 carbon atoms, a halogen atom, a cyano group, a nitro group, —S(R)O$_2$, or —S(R)O, wherein R represents a substituent, and neighboring groups among $R_{31}$ and $R_{32}$, $R_{32}$ and $R_{33}$, and $R_{33}$ and $R_{34}$ may be linked to each other to form a saturated or unsaturated ring structure.

2. An organic electroluminescence device comprising at least one organic thin film layer comprising a light emitting layer between an anode and a cathode, wherein the at least one organic thin film layer comprises the metal complex compound of claim 1.

3. The organic electroluminescence device according to claim 2, wherein said light emitting layer comprises said metal complex compound as a light emitting material.

4. The organic electroluminescence device according to claim 2, wherein said light emitting layer comprises said metal complex compound as a dopant.

5. The organic electroluminescence device according to claim 2, wherein said device comprises at least one of an electron injecting layer and an electron transporting layer between said light emitting layer and the cathode, and at least one of the electron injecting layer and the electron transporting layer contains a π-electron deficiency nitrogen-containing heterocyclic derivative.

6. The organic electroluminescence device according to claim 2, wherein a reductive dopant is added in an interface area between the cathode and the at least one organic thin film layer.

* * * * *